(12) United States Patent
Kowshik

(10) Patent No.: US 11,273,290 B2
(45) Date of Patent: Mar. 15, 2022

(54) FLEXIBLE INSTRUMENT WITH NESTED CONDUITS

(71) Applicant: Intuitive Surgical Operations, Inc., Sunnyvale, CA (US)

(72) Inventor: Anoop B. Kowshik, San Jose, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 435 days.

(21) Appl. No.: 14/844,341

(22) Filed: Sep. 3, 2015

(65) Prior Publication Data

US 2016/0067450 A1 Mar. 10, 2016

Related U.S. Application Data

(60) Provisional application No. 62/048,536, filed on Sep. 10, 2014.

(51) Int. Cl.
*A61M 25/01* (2006.01)
*A61B 17/00* (2006.01)
(Continued)

(52) U.S. Cl.
CPC ......... *A61M 25/0147* (2013.01); *A61B 34/30* (2016.02); *A61B 34/35* (2016.02);
(Continued)

(58) Field of Classification Search
CPC ............... A61B 1/0051; A61B 1/0058; A61B 2034/301; A61B 2017/003; A61B 34/71; A61B 2034/715; A61B 34/76; A61B 34/35; A61B 34/30; A61B 2090/371; A61B 2034/2051; A61B 2034/306;
(Continued)

(56) References Cited

U.S. PATENT DOCUMENTS 6,380,732 B1  4/2002  Gilboa
6,389,187 B1  5/2002  Greenaway et al.
(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Michael J Carey
*Assistant Examiner* — Genja M Frankert
(74) *Attorney, Agent, or Firm* — Haynes and Boone, LLP

(57) ABSTRACT

A medical instrument includes a nested conduit extending through an elongate flexible body. A tendon extends through an inner lumen of the inner conduit. A first control element is coupled to the outer conduit and a second control element is coupled to the inner conduit. Each of the first and second control elements is adjustable between a first state and a second state. The outer conduit is axially constrained proximate the first control element in the first state of the first control element and is not axially constrained in the second state. The inner conduit is axially constrained proximate the second control element in the first state of the second control element and is not axially constrained in the second state. An articulatable length of the nested conduit is variable based on adjustment between the first and second states of the first control element and the second control element.

20 Claims, 13 Drawing Sheets

(51) Int. Cl.
*A61B 34/35* (2016.01)
*A61B 34/00* (2016.01)
*A61B 34/30* (2016.01)
A61B 90/00 (2016.01)
A61B 34/20 (2016.01)

(52) U.S. Cl.
CPC .............. *A61B 34/71* (2016.02); *A61B 34/76* (2016.02); *A61M 25/0138* (2013.01); A61B 2034/2051 (2016.02); A61B 2034/2061 (2016.02); A61B 2034/301 (2016.02); A61B 2034/306 (2016.02); A61B 2090/066 (2016.02); A61B 2090/3614 (2016.02); A61B 2090/371 (2016.02)

(58) Field of Classification Search
CPC ...... A61B 2034/2061; A61B 2090/066; A61B 1/00078; A61M 25/0141; A61M 25/0147; A61M 25/0138
See application file for complete search history.

(56) References Cited

U.S. PATENT DOCUMENTS

| | | | | |
|---|---|---|---|---|
| 8,251,977 | B2* | 8/2012 | Partlett | A61M 25/0105 604/523 |
| 2002/0068868 | A1* | 6/2002 | Thompson | A61M 25/0136 600/434 |
| 2002/0161281 | A1* | 10/2002 | Jaffe | A61B 1/0008 600/114 |
| 2003/0018318 | A1* | 1/2003 | Melsky | A61M 25/0138 604/526 |
| 2003/0045778 | A1* | 3/2003 | Ohline | A61B 1/0053 600/114 |
| 2003/0171775 | A1* | 9/2003 | Belson | A61B 17/00234 606/213 |
| 2004/0122360 | A1* | 6/2004 | Waldhauser | A61M 25/0012 604/95.04 |
| 2004/0242966 | A1* | 12/2004 | Barry | A61B 1/0055 600/146 |
| 2005/0070844 | A1* | 3/2005 | Chow | A61M 25/0012 604/95.04 |
| 2006/0013523 | A1 | 1/2006 | Childlers et al. | |
| 2007/0260225 | A1* | 11/2007 | Sakakine | A61M 25/0136 604/528 |
| 2007/0270679 | A1* | 11/2007 | Nguyen | A61M 25/0043 600/373 |
| 2007/0282358 | A1* | 12/2007 | Remiszewski | A61B 17/00 606/159 |
| 2009/0043372 | A1* | 2/2009 | Northrop | A61M 25/0013 623/1.15 |
| 2009/0062606 | A1* | 3/2009 | Ueda | A61B 1/00154 600/114 |
| 2009/0099420 | A1* | 4/2009 | Woodley | A61B 1/0053 600/142 |
| 2009/0137875 | A1* | 5/2009 | Kitagawa | A61B 1/0052 600/146 |
| 2009/0240110 | A1* | 9/2009 | Miyawaki | A61B 1/00078 600/149 |
| 2010/0280320 | A1* | 11/2010 | Alvarez | A61B 17/00234 600/146 |
| 2010/0280449 | A1* | 11/2010 | Alvarez | A61B 17/00234 604/95.04 |
| 2010/0331820 | A1* | 12/2010 | Prisco | A61B 1/0052 604/528 |
| 2011/0106055 | A1* | 5/2011 | Robertson | A61B 1/00078 604/525 |
| 2011/0137309 | A1* | 6/2011 | Ogle | A61M 25/0136 606/41 |
| 2011/0319714 | A1* | 12/2011 | Roelle | A61B 1/00006 600/118 |
| 2012/0123441 | A1* | 5/2012 | Au | A61B 34/30 606/130 |
| 2012/0265016 | A1* | 10/2012 | Katsura | A61B 1/00071 600/146 |
| 2012/0289777 | A1 | 11/2012 | Chopra et al. | |
| 2013/0096384 | A1* | 4/2013 | Arai | A61B 1/0055 600/144 |
| 2013/0178705 | A1* | 7/2013 | Takeuchi | A61B 1/0052 600/144 |
| 2013/0197563 | A1* | 8/2013 | Saab | A61M 29/02 606/191 |
| 2013/0296781 | A1* | 11/2013 | Tegg | A61M 25/0147 604/95.04 |
| 2013/0317519 | A1* | 11/2013 | Romo | A61B 34/30 606/130 |
| 2014/0142387 | A1* | 5/2014 | Wimmer | A61B 1/00071 600/138 |
| 2014/0148759 | A1* | 5/2014 | Macnamara | A61M 25/0147 604/95.04 |
| 2014/0371764 | A1* | 12/2014 | Oyola | B25J 18/06 606/130 |
| 2015/0359416 | A1* | 12/2015 | Simchony | A61B 1/0055 600/562 |
| 2015/0374211 | A1* | 12/2015 | Smith | A61B 1/00078 600/114 |
| 2016/0310701 | A1* | 10/2016 | Pai | A61M 25/0138 |

* cited by examiner

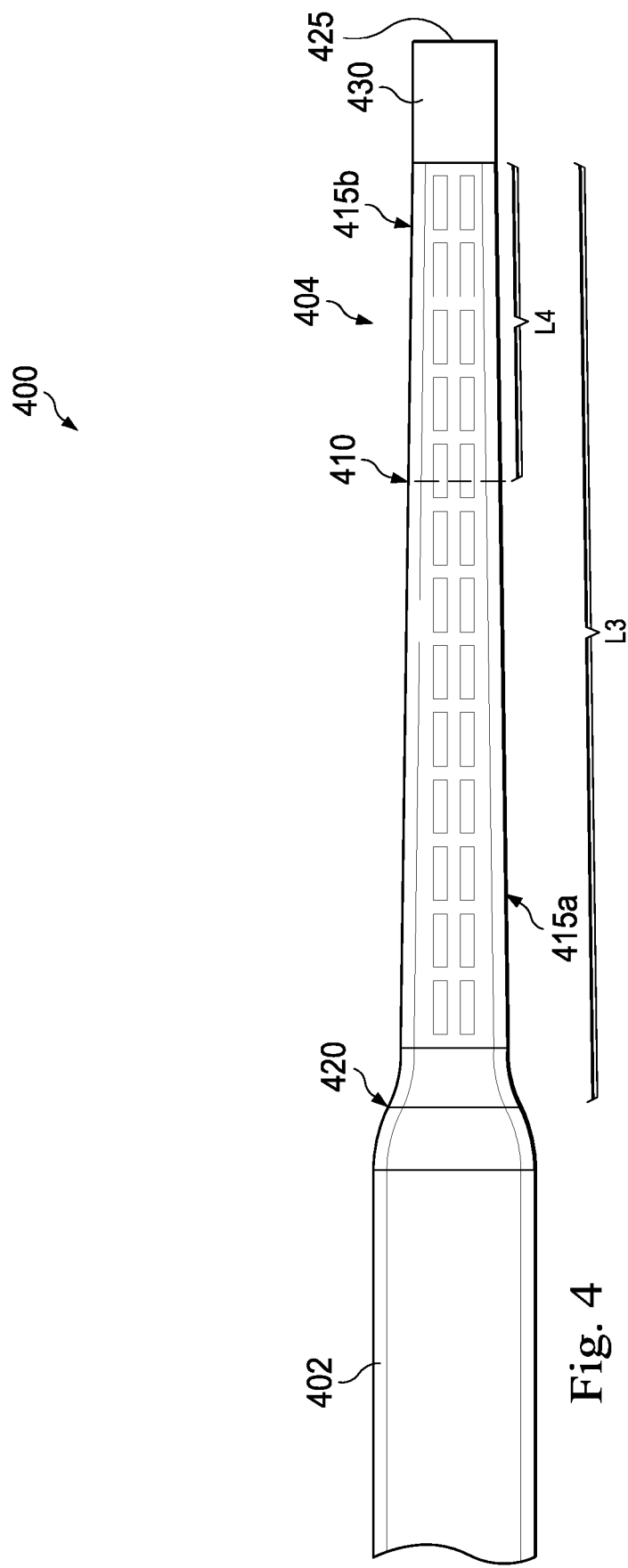

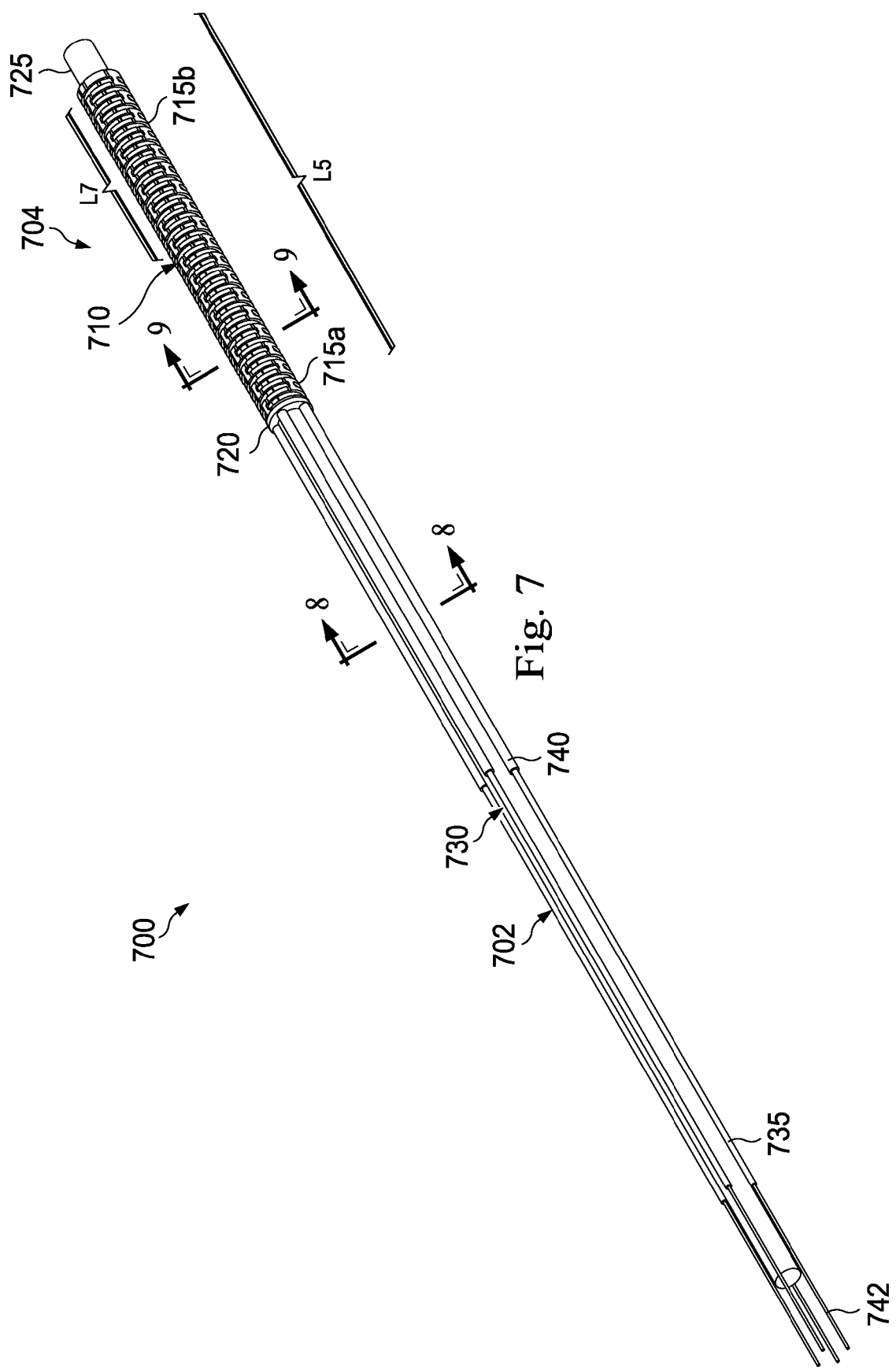

FLEXIBLE INSTRUMENT WITH NESTED CONDUITS

RELATED APPLICATIONS

This patent application claims priority to and the benefit of the filing date of U.S. Provisional Patent Application 62/048,536, entitled "FLEXIBLE INSTRUMENT WITH NESTED CONDUITS," filed Sep. 10, 2014, which is incorporated by reference herein in its entirety.

FIELD

The present disclosure is directed to systems and methods for navigating a patient anatomy to conduct a minimally invasive procedure, and more particularly to apparatus and methods for steering a low-profile, flexible interventional instrument into a patient anatomy.

BACKGROUND

Minimally invasive medical techniques are intended to reduce the amount of tissue that is damaged during interventional procedures, thereby reducing patient recovery time, discomfort, and deleterious side effects. Such minimally invasive techniques may be performed through natural orifices in a patient anatomy or through one or more surgical incisions. Through these natural orifices or incisions clinicians may insert interventional instruments (including surgical, diagnostic, therapeutic, or biopsy instruments) to reach a target tissue location. To reach the target tissue location, a minimally invasive interventional instrument may navigate natural or surgically created passageways in anatomical systems such as the lungs, the colon, the intestines, the kidneys, the heart, the circulatory system, or the like. Some minimally invasive medical instruments may be teleoperated or otherwise computer-assisted.

Telerobotic interventional instruments may be used to navigate through the patient anatomy, and such instruments need to be small enough and flexible enough to physically fit within those anatomical lumens. In some applications, it is desirable to have different articulable lengths of the instrument to allow for greater maneuverability and ease of use during the procedure. In some instances, this may be achieved with additional articulation motors and/or a telescoping instrument. However, manufacturing a flexible telerobotic instrument with distinct articulable sections that is sized to contain the mechanical structures suitable for remote or telerobotic operation and that has an outer diameter that is sufficiently small to navigate very small passageways can be challenging. Improved devices and systems are needed for telerobotic surgical instruments configured for insertion into anatomical or surgically-created passageways, especially very small passageways.

SUMMARY

The embodiments of the invention are summarized by the claims that follow the description.

In one exemplary aspect, the present disclosure is directed to a medical instrument comprising an elongate flexible body including a proximal section and a steerable distal section. The instrument also comprises a control tendon extending within the elongate flexible body. The instrument also comprises an axially variable stiffening mechanism including a first conduit extending through a second conduit. The axially variable stiffening mechanism is adjustable between a first state in which an actuation of the control tendon produces a first bend radius in the steerable distal section and a second state in which the actuation of the control tendon produces a second bend radius in the steerable distal section. The second bend radius is different than the first bend radius.

In another exemplary aspect, the present disclosure is directed to a minimally invasive medical instrument comprising an elongate flexible body including a proximal portion, a distal portion, and a distal end. The instrument also includes a plurality of tendons extending from the proximal portion through the distal portion of the elongate flexible body. Each tendon is actuatable to bend the distal portion. The instrument also includes a plurality of nested conduits extending through the elongate flexible body and a plurality of control elements, each coupled to one of the plurality of nested conduits. Each of the control elements is adjustable between a first state configured to increase the axial stiffness of the coupled conduit and a second state configured to decrease the axial stiffness of the coupled conduit.

In another exemplary aspect, a minimally invasive medical system comprises an actuator and an elongate flexible body including a proximal portion, a distal portion, and a distal end. The system also includes a plurality of nested conduits extending through the elongate flexible body. Each nested conduit comprises a first conduit including a first lumen and a second conduit including a second lumen configured to receive the first conduit. The system also includes a plurality of actuation tendons. Each actuation tendon is fixed at a proximal end relative to the actuator and extending through the first lumen of one of the plurality of first conduits into the distal portion. The plurality of actuation tendons are actuatable to bend the distal portion. The system also includes a first control element in contact with at least one first conduit. The first control element includes a first state configured to increase the axial stiffness of the at least one first conduit.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 4 illustrates an exemplary catheter system according to one embodiment of the present disclosure.

FIG. 7 illustrates a perspective, partially cut-away view of an exemplary catheter system according to one embodiment of the present disclosure.

DETAILED DESCRIPTION

Figure 1:
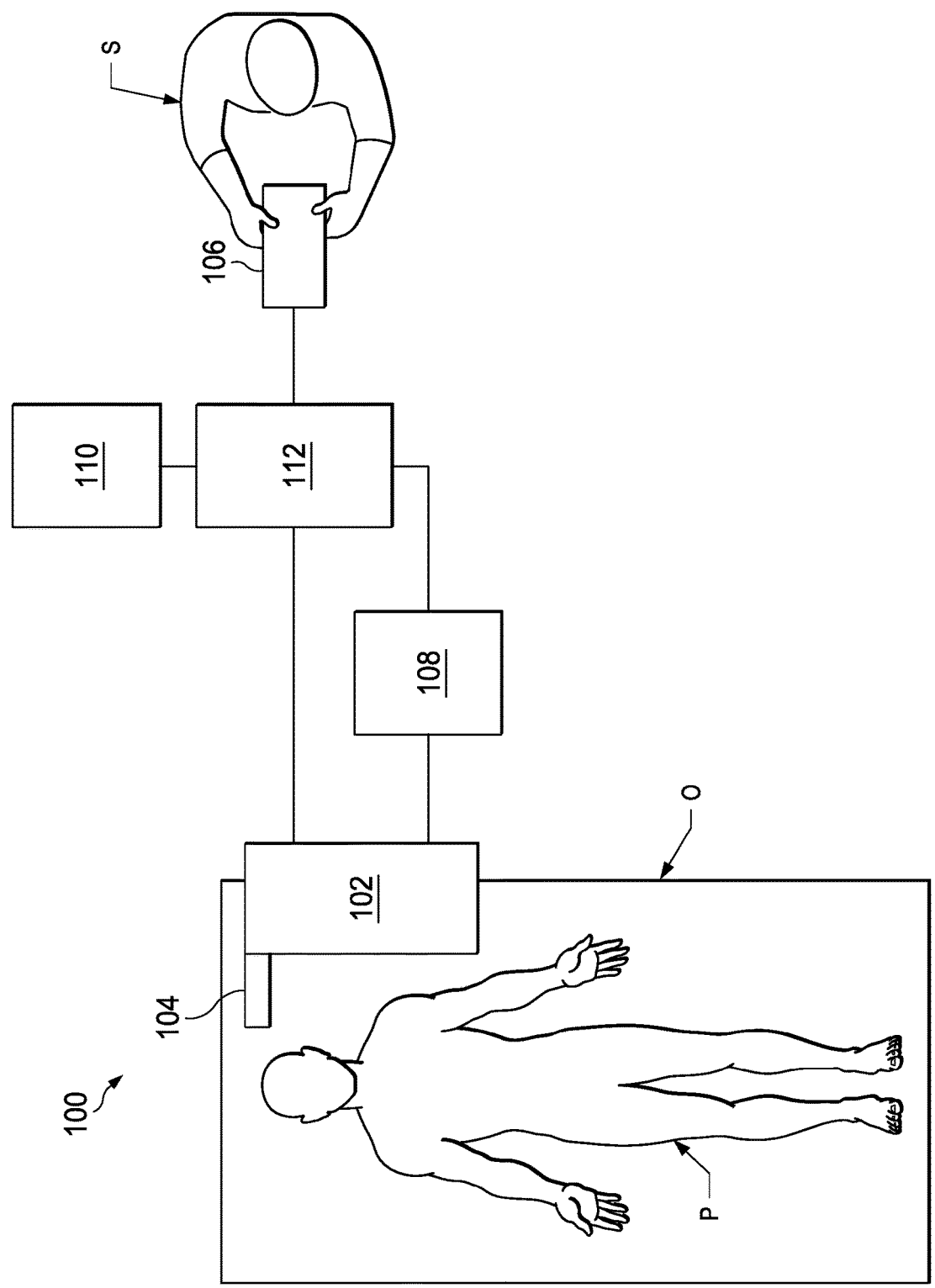
FIG. 1 illustrates a telerobotic interventional system in accordance with an embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an elongated object.

It will be appreciated that the terms "proximal" and "distal" are used herein with reference to a clinician manipulating an end of an instrument extending from the clinician to a surgical or diagnostic site. The term "proximal" refers to the portion of the instrument closer to the clinician, and the term "distal" refers to the portion of the instrument further away from the clinician and closer to the surgical or diagnostic site. For conciseness and clarity, spatial terms such as "horizontal," "vertical," "above," and "below" may be used herein with respect to the drawings. However, surgical and diagnostic instruments are used in many orientations and positions, and there terms are not intended to be limiting and absolute.

The present disclosure relates generally to steerable conduits or tubes for actuation cables used in the operation of articulating devices. In some instances, embodiments of the present disclosure are configured to be part of a telerobotic system. Those of skill in the art will realize that the steerable conduits disclosed herein may be utilized in similar (e.g., non-telerobotic) applications requiring a steerable distal tip.

The steerable conduits disclosed herein are formed of a flexible material and are configured to carry actuation/control cables or tendons. The walls of the steerable conduits disclosed herein include channels that are shaped and configured to carry the cables/tendons. The steerable conduits disclosed herein comprise nested conduits that run coaxially with respect to each other along at least a portion of the articulating device. In some embodiments, the articulable devices include a cable/tendon running through a first conduit, which runs through a second conduit having a larger cross-sectional diameter than the first conduit. By having the cables/tendons resting within these nested conduits or tubes, the articulable devices disclosed herein are capable of at least two different articulable lengths without requiring additional articulation motors and/or a telescoping design. Thus, the nested conduits disclosed herein may improve the flexibility and performance of steerable portions of articulating devices, and may increase the range of suitable applications for articulating devices utilizing such steerable conduits.

According to various embodiments, medical procedures, such as biopsy procedures, may be performed using a teleoperational system to guide instrument delivery. Referring to FIG. 1 of the drawings, a teleoperational medical system for use in, for example, medical procedures including diagnostic, therapeutic, or surgical procedures, is generally indicated by the reference numeral 100. As will be described, the teleoperational medical systems of this disclosure are under the teleoperational control of a surgeon. In alternative embodiments, a teleoperational medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures. As shown in FIG. 1, the teleoperational medical system 100 generally includes a teleoperational assembly 102 mounted to or near an operating table O on which a patient P is positioned. A medical instrument system 104 is operably coupled to the teleoperational assembly 102. An operator input system 106 allows a surgeon or other type of clinician S to view images of or representing the surgical site and to control the operation of the medical instrument system 104.

The operator input system 106 may be located at a surgeon's console, which is usually located in the same room as operating table O. It should be understood, however, that the surgeon S can be located in a different room or a completely different building from the patient P. Operator input system 106 generally includes one or more control device(s) for controlling the medical instrument system 104. The control device(s) may include one or more of any number of a variety of input devices, such as hand grips, joysticks, trackballs, data gloves, trigger-guns, hand-operated controllers, voice recognition devices, touch screens, body motion or presence sensors, and the like. In some embodiments, the control device(s) will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device (s) are manual input devices which move with six degrees of freedom, and which may also include an actuatable handle for actuating instruments (for example, for closing grasping jaws, applying an electrical potential to an electrode, delivering a medicinal treatment, and the like).

The teleoperational assembly 102 supports the medical instrument system 104 and may include a kinematic structure of one or more non-servo controlled links (e.g., one or more links that may be manually positioned and locked in place, generally referred to as a set-up structure) and a teleoperational manipulator. The teleoperational assembly 102 includes plurality of motors that drive inputs on the medical instrument system 104. These motors move in response to commands from the control system (e.g., control system 112). The motors include drive systems which when coupled to the medical instrument system 104 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like.

The teleoperational medical system 100 also includes a sensor system 108 with one or more sub-systems for receiving information about the instruments of the teleoperational assembly. Such sub-systems may include a position sensor system (e.g., an electromagnetic (EM) sensor system); a shape sensor system for determining the position, orientation, speed, velocity, pose, and/or shape of the catheter tip and/or of one or more segments along a flexible body of instrument system 104; and/or a visualization system for capturing images from the distal end of the catheter system.

The teleoperational medical system 100 also includes a display system 110 for displaying an image or representation of the surgical site and medical instrument system(s) 104 generated by sub-systems of the sensor system 108. The display 110 and the operator input system 106 may be oriented so the operator can control the medical instrument system 104 and the operator input system 106 with the perception of telepresence.

Alternatively or additionally, display system 110 may present images of the surgical site recorded and/or imaged preoperatively or intra-operatively using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and the like. The presented preoperative or intra-operative images may include two-dimensional, three-dimensional, or four-dimensional (including e.g., time based or velocity based information) images and associated image data sets for reproducing the images.

In some embodiments, the display system 110 may display a virtual visualization image in which the actual location of the medical instrument is registered (e.g., dynamically referenced) with preoperative or concurrent images to present the surgeon with a virtual image of the internal surgical site at the location of the tip of the medical instrument.

In other embodiments, the display system 110 may display a virtual visualization image in which the actual location of the medical instrument is registered with prior images (including preoperatively recorded images) or concurrent images to present the surgeon with a virtual image of a medical instrument at the surgical site. An image of a portion of the medical instrument system 104 may be superimposed on the virtual image to assist the surgeon controlling the medical instrument.

The teleoperational medical system 100 also includes a control system 112. The control system 112 includes at least one memory and at least one processor (not shown), and typically a plurality of processors, for effecting control between the medical instrument system 104, the operator input system 106, the sensor system 108, and the display system 110. The control system 112 also includes programmed instructions (e.g., a computer-readable medium storing the instructions) to implement some or all of the methods described in accordance with aspects disclosed herein. While control system 112 is shown as a single block in the simplified schematic of FIG. 1, the system may include two or more data processing circuits with one portion of the processing optionally being performed on or adjacent the teleoperational assembly 102, another portion of the processing being performed at the operator input system 106, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may include one or more servo controllers that receive force and/or torque feedback from the medical instrument system 104. Responsive to the feedback, the servo controllers transmit signals to the operator input system 106. The servo controller(s) may also transmit signals instructing teleoperational assembly 102 to move the medical instrument system(s) 104 which extend into an internal surgical site within the patient body via openings in the body. Any suitable conventional or specialized servo controller may be used. A servo controller may be separate from, or integrated with, teleoperational assembly 102. In some embodiments, the servo controller and teleoperational assembly are provided as part of a teleoperational arm cart positioned adjacent to the patient's body.

The control system 112 may further include a virtual visualization system to provide navigation assistance to the medical instrument system(s) 104. Virtual navigation using the virtual visualization system is based upon reference to an acquired dataset associated with the three dimensional structure of the anatomical passageways. More specifically, the virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software is used to convert the recorded images into a two dimensional or three dimensional composite representation of a partial or an entire anatomical organ or anatomical region. An image data set is associated with the composite representation. The composite representation and the image data set describe the various locations and shapes of the passageways and their connectivity. The images used to generate the composite representation may be recorded preoperatively or intra-operatively during a clinical procedure. In an alternative embodiment, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, the sensor system 108 may be used to compute an approximate location of the instrument with respect to the patient anatomy. The location can be used to produce both macro-level tracking images of the patient anatomy and virtual internal images of the patient anatomy. Various systems for using fiber optic sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomical Structure for Image-Guided Surgery") which is incorporated by reference herein in its entirety, discloses one such system.

The teleoperational medical system 100 may further include optional operation and support systems (not shown) such as illumination systems, steering control systems, irrigation systems, and/or suction systems. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated, or they may be positioned in separate locations. Multiple operator input systems allow more than one operator to control one or more manipulator assemblies in various combinations.

Figure 2:
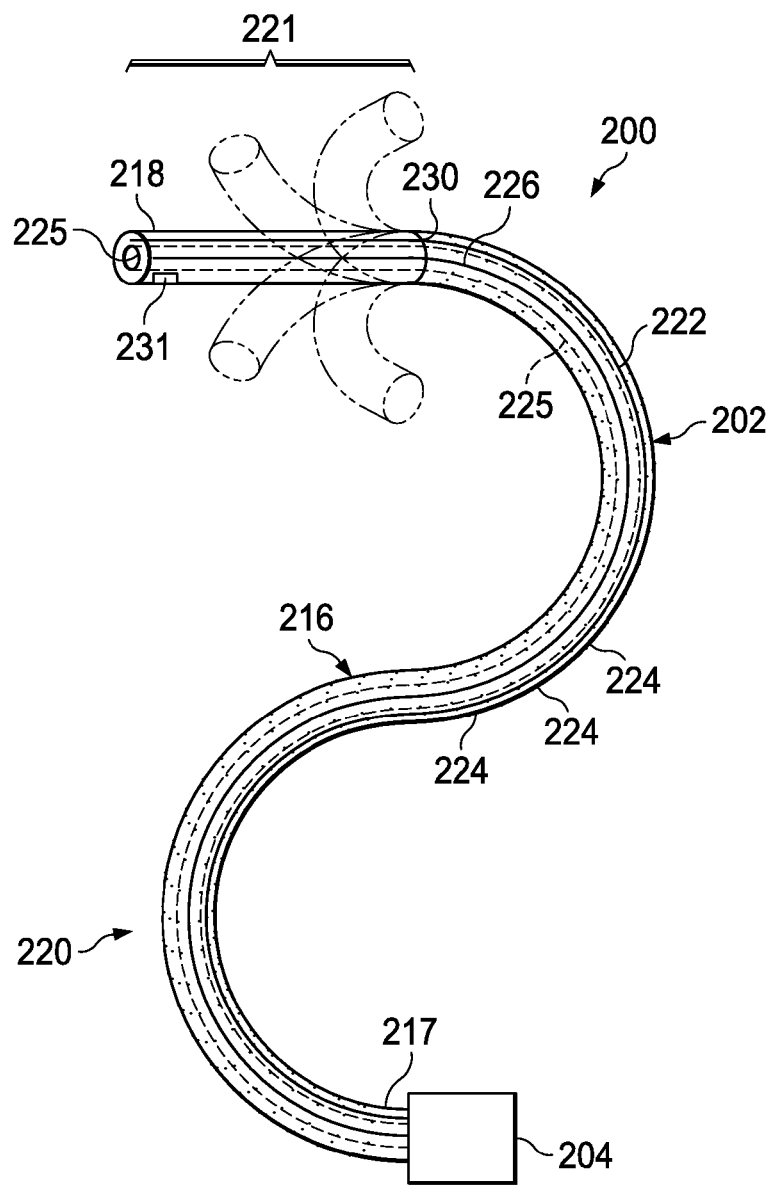
FIG. 2 illustrates an interventional instrument system in accordance with an embodiment of the present disclosure.

FIG. 2 illustrates an interventional instrument system 200 which may be used as the interventional instrument system 104 of the telerobotic interventional system 100. Alternatively, the interventional instrument system 200 may be used for non-robotic exploratory procedures or in procedures involving traditional manually operated interventional instruments, such as endoscopy. In various embodiments, the interventional instrument system 200 may include a flexible bronchial instrument, such as a bronchoscope or bronchial catheter for use in examination, diagnosis, biopsy, or treatment of a lung. The system is also suited for navigation and treatment of other tissues, via natural or surgically created connected passageways, in any of a variety of anatomical systems including the colon, the intestines, the kidneys, the brain, the heart, the circulatory system, or the like.

The instrument system 200 includes a catheter system 202 coupled to an instrument body 204. The catheter system 202 includes an elongated flexible body 216 having a proximal end 217 and a distal end or tip portion 218. A distal portion 221 extends between the distal end 218 and a transition section 230. In some embodiments, there may be more than one transition section 230 along the length of the flexible body 216. In some embodiments, as described in greater detail below with reference to FIG. 3A, at least one set of conduits for actuation cables terminates at the transition section 230.

A proximal portion 220 extends between the transition section 230 and the proximal end 217. In one embodiment, the flexible body 216 has an approximately 3 mm outer diameter. Other flexible body outer diameters may be larger or smaller. In some embodiments, the flexible body outer diameter tapers from the proximal end 217 to the distal end 218. For example, the flexible body outer diameter at the proximal end 217 may be greater than the flexible body outer diameter at the distal end 218. In some embodiments, the flexible body outer diameter is substantially unchanged throughout the proximal portion 220. In some embodiments, the flexible body outer diameter is substantially unchanged throughout the distal portion 221. In other embodiments, the flexible body outer diameter may taper throughout the proximal portion 220 and/or the distal portion 221. In other embodiments, there can be an abrupt change or stop in the flexible body 216 at the transition section 230 from a larger outer diameter of the proximal portion 220 to a smaller diameter of the distal portion 221.

The catheter system 202 may optionally include a shape sensor 222 for determining the position, orientation, speed, pose, and/or shape of the catheter tip at distal end 218 and/or of one or more segments 224 along the body 216. The entire length of the body 216 between the distal end 218 and the proximal end 217 may be effectively divided into the segments 224. If the instrument system 200 is an interventional instrument system 104 of the telerobotic interventional system 100, the shape sensor 222 may be a component of the sensor system 108. If the instrument system 200 is manually operated or otherwise used for non-robotic procedures, the shape sensor 222 may be coupled to a tracking system that interrogates the shape sensor and processes the received shape data.

The shape sensor system 222 may include an optical fiber aligned with the flexible catheter body 216 (e.g., provided within an interior channel (not shown) or mounted externally). The optical fiber of the shape sensor system 222 may form a fiber optic bend sensor for determining the shape of at least a portion of the catheter system 202. Various systems and methods for monitoring the shape and relative position of an optical fiber in three dimensions are described in U.S. patent application Ser. No. 11/180,389, filed Jul. 13, 2005, disclosing "Fiber optic position and shape sensing device and method relating thereto;" U.S. Provisional Pat. App. No. 60/588,336, filed on Jul. 16, 2004, disclosing "Fiber-optic shape and relative position sensing;" and U.S. Pat. No. 6,389,187, filed on Jun. 17, 1998, disclosing "Optical Fibre Bend Sensor," which are incorporated by reference herein in their entireties. In other alternatives, sensors employing other strain sensing techniques such as Rayleigh scattering, Raman scattering, Brillouin scattering, and Fluorescence scattering may be suitable. In other alternative embodiments, the shape of the catheter may be determined using other techniques.

More specifically, light passing through the optical fiber is processed to detect the shape of the catheter system 202 and for utilizing that information to assist in surgical procedures. The sensor system (e.g. sensor system 108 or another type of tracking system as described in FIG. 3A) may include an interrogation system for generating and detecting the light used for determining the shape of the catheter system 202. This information, in turn, in can be used to determine other related variables, such as velocity and acceleration of the parts of an interventional instrument.

The flexible catheter body 216 includes a lumen 225 sized and shaped to receive an auxiliary tool 226. Auxiliary tools may include, for example, image capture probes, biopsy devices, laser ablation fibers, or other surgical, diagnostic, or therapeutic tools. Auxiliary tools may include end effectors having a single working member such as a scalpel, a blade, an optical fiber, or an electrode. Other end effectors may include pair or plurality of working members such as forceps, graspers, scissors, or clip appliers, for example. Examples of electrically activated end effectors include electrosurgical electrodes, transducers, sensors, and the like. Other embodiments may lack a lumen 225.

In various embodiments, the auxiliary tool 226 may be an image capture probe including a tip portion with a stereoscopic or monoscopic camera disposed near the distal end 218 of the flexible catheter body 216 for capturing images (including video images) that are processed for display. The image capture probe may include a cable coupled to the camera for transmitting the captured image data. Alternatively, the image capture instrument may be a fiber-optic bundle, such as a fiberscope, that couples to the imaging system. The image capture instrument may be single or multi-spectral, for example capturing image data in the visible spectrum, or capturing image data in the visible and infrared or ultraviolet spectrums.

The catheter system 202 may optionally include a position sensor system 231 (e.g., an electromagnetic (EM) sensor system) which may be disabled by an operator or an automated system (e.g., a function of the control system 112) if it becomes unreliable due to, for example, magnetic interference from other equipment in the surgical suite or if other navigation tracking systems are more reliable. The position sensor system 231 may be an EM sensor system that includes one or more conductive coils that may be subjected to an externally generated electromagnetic field. Each coil of the EM sensor system 231 then produces an induced electrical signal having characteristics that depend on the position and orientation of the coil relative to the externally generated electromagnetic field. In one embodiment, the EM sensor system may be configured and positioned to measure six degrees of freedom ("6-DOF"), e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of an EM sensor system is provided in U.S. Pat. No. 6,380,732, filed Aug. 11, 1999, disclosing "Six-Degree of Freedom Tracking System Having a Passive Transponder on the Object Being Tracked," which is incorporated by reference herein in its entirety.

The flexible catheter body 216 may also house actuation cables, linkages, or other steering controls (not shown in FIG. 2) that extend between the instrument body 204 and the distal end 218 to controllably bend or turn the distal portion 221 as shown for example by the dotted line versions of the distal portion. In some embodiments, the flexible body 216 can define one or more additional lumens through which interventional instruments, cables, linkages, and/or other steering controls (such as, by way of non-limiting example, coil pipes and tendons) may extend.

In embodiments in which the instrument system 200 is actuated by a telerobotic assembly, the instrument body 204 may include drive inputs that couple to motorized drive elements of the telerobotic assembly. In embodiments in which the instrument system 200 is manually operated, the instrument body 204 may include gripping features, manual actuators, and other components for manually controlling the motion of the instrument system. The catheter system may be steerable or, alternatively, may be non-steerable with no integrated mechanism for operator control of the instrument bending. In some embodiments, the proximal portion 220 is configured to passively deflect in response to forces acting upon the flexible body, and the distal portion 221 is configured to actively articulate in response to the telerobotic assembly and/or control signals from the instrument body 204.

Figure 3A:
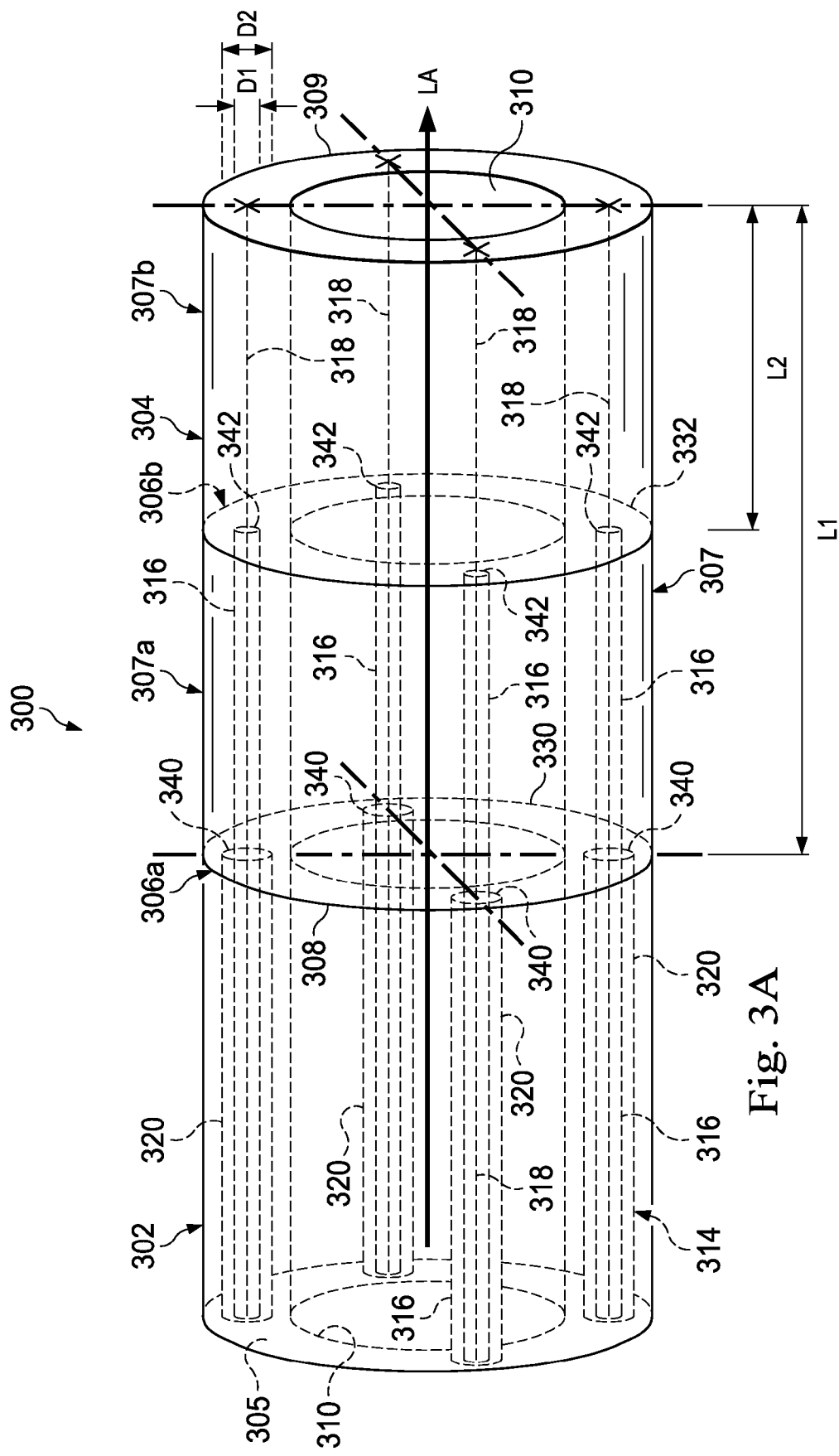
FIG. 3A illustrates an exemplary catheter system, showing relative positions of various elements that enable articulation of the system, in accordance with an embodiment of the present disclosure.

FIG. 3A illustrates a portion of a catheter system 300 having a proximal portion 302, a distal portion 304, a wall 305, a proximal transition section 306a disposed between the proximal portion 302 and the distal portion 304, and a distal transition section 306b disposed in the distal portion 304. The catheter system 300 may be the same as the catheter system 202 described above in relation to FIG. 2. The proximal portion 302 may be the same as a distal-most segment 224 of the proximal portion 220 and the distal portion 304 may be the same as a proximal-most segment 224 of the distal portion 221 of the catheter system 202. In some embodiments, the transition section 306a is the same as the transition section 230 shown between the proximal portion 220 and the distal portion 221 shown in FIG. 2. In the pictured embodiment, the distal portion 304 includes a steerable segment 307, which includes a proximal steerable portion or first bendable portion 307a and a distal steerable portion or second bendable portion 307b. The steerable segment 307 includes a proximal end 308 and a distal end 309. The proximal steerable portion 307a extends from the proximal transition section 306a to the distal transition section 306b, and the proximal steerable portion 307b extends from the distal transition section 306b to the distal end 309. Other embodiments may include more transition sections within the distal portion 304.

A lumen 310 (e.g., which may be the same as the lumen 225 shown in FIG. 2) extends centrally through the proximal portion 302, the transition sections 306a, 306b, and the distal portion 304 of the catheter system 300. The transition sections 306a, 306b may include flexible walls with layered wall components and/or plate-like structures that are omitted from the illustration of FIG. 3A for the sake of clarity.

Cable assemblies 314 extend down the length of a catheter flexible body (e.g., flexible body 216) of the catheter system 300 to the distal portion 304. In some embodiments, the cable assemblies 314 have similar characteristics to a Bowden cable, which is a type of flexible cable used to transmit mechanical force or energy by the movement of an inner cable relative to a hollow outer cable housing such as, without limitation, a helical coil pipe. In the pictured embodiment, four cable assemblies 314 are arranged circumferentially in the wall 305 around the lumen 310. Other embodiments may include any number of cable assemblies 314 arranged in any of a variety of symmetrical or asymmetrical patterns within the wall 305.

In this embodiment, the cable assemblies 314 extend entirely within or at least partially within the wall 305 of the catheter system 300. The cable assemblies 314 comprise multiple sets of nested conduits or coil pipes 316 through which control wires or tendons 318 extend. In some embodiments, the conduits or coil pipes described herein may comprise helically-wound tubular housings defining a passageway, including, without limitation, a cylindrical tube formed of a single, tightly wound wire and a cylindrical tube formed of several wire strands running in a multiple helix. In other embodiments, the conduits or coil pipes described herein may comprise any tubular housing that is flexible and axially compressible, such as, without limitation, a cylindrical tube having a braided or woven wall construction. In the pictured embodiment, each cable assembly 314 comprises an inner coil pipe 316 nested within an outer coil pipe 320. In the present disclosure, "nested" refers to a concentric arrangement of tubes having different diameters that are coaxially aligned about a common longitudinal axis. For example, an inner tube may be nested within an outer tube having a large outer diameter than the inner tube, and the inner and outer tubes may be axially movable relative to each other. The space between the inner and outer tubes may be fluid-filled (e.g., air-filled), or may be filled with an insulating or imaging material that does not limit the axial translation of the tubes relative to each other.

The inner and outer coil pipes 316, 320 form an axially variable stiffening mechanism that is configured to isolate the articulation or bending motion of the catheter system 300 to the distal portion 304. The inner coil pipe 316 and the outer coil pipe 320 comprise flexible conduits for the tendons 318. The coil pipes 316, 320 are axially compressible until loading on the coil pipes causes the helical coils to touch. When the helical coils contact each other, the coil pipes become non-compressible and rigid. The inner coil pipe 316 and the outer coil pipe 320 are coaxially aligned along the length of the catheter system 300. The inner coil pipe 316 houses the tendon 318 along the length of the flexible body, and the tendon 318 can slide longitudinally within the inner coil pipe 316. Similarly, the outer coil pipe 320 houses the inner coil pipe 316 along the length of the flexible body, and the inner coil pipe 316 can slide longitudinally within the outer coil pipe 320. Each set of coil pipes is fixed or terminated at distal and proximal ends. The inner coil pipes 316 terminate at the distal transition section 306b, proximal to the distal steerable portion 307b within the distal portion 304. The outer coil pipes 320 terminate at the proximal transition section 306a, proximal to the entire steerable section 307, including both the proximal steerable portion 307a and the distal steerable portion 307b. The tendons 318 extend out of the coil pipes 316 at the distal transition section 306b at or distal to the distal transition section 306b, extend through the distal steerable portion 307b, and attach to the distal end 309.

The inner coil pipes 316 include an outer diameter D1 that is smaller than an inner diameter D2 of the outer coil pipes 320. In some embodiments, the outer diameter D1 of the inner coil pipes 316 ranges from 0.010-0.011 inches, with an inner diameter ranging from 0.008-0.009 inches. In some embodiments, the inner diameter D2 of the outer coil pipes 320 ranges from 0.012-0.014 inches, with an inner diameter ranging from 0.010-0.012 inches. In some embodiments, the tendons 318 are 0.007 inches thick. These measurements are provided for exemplary purposes and are not intended to be limiting. Other dimensions are contemplated.

Figure 9:
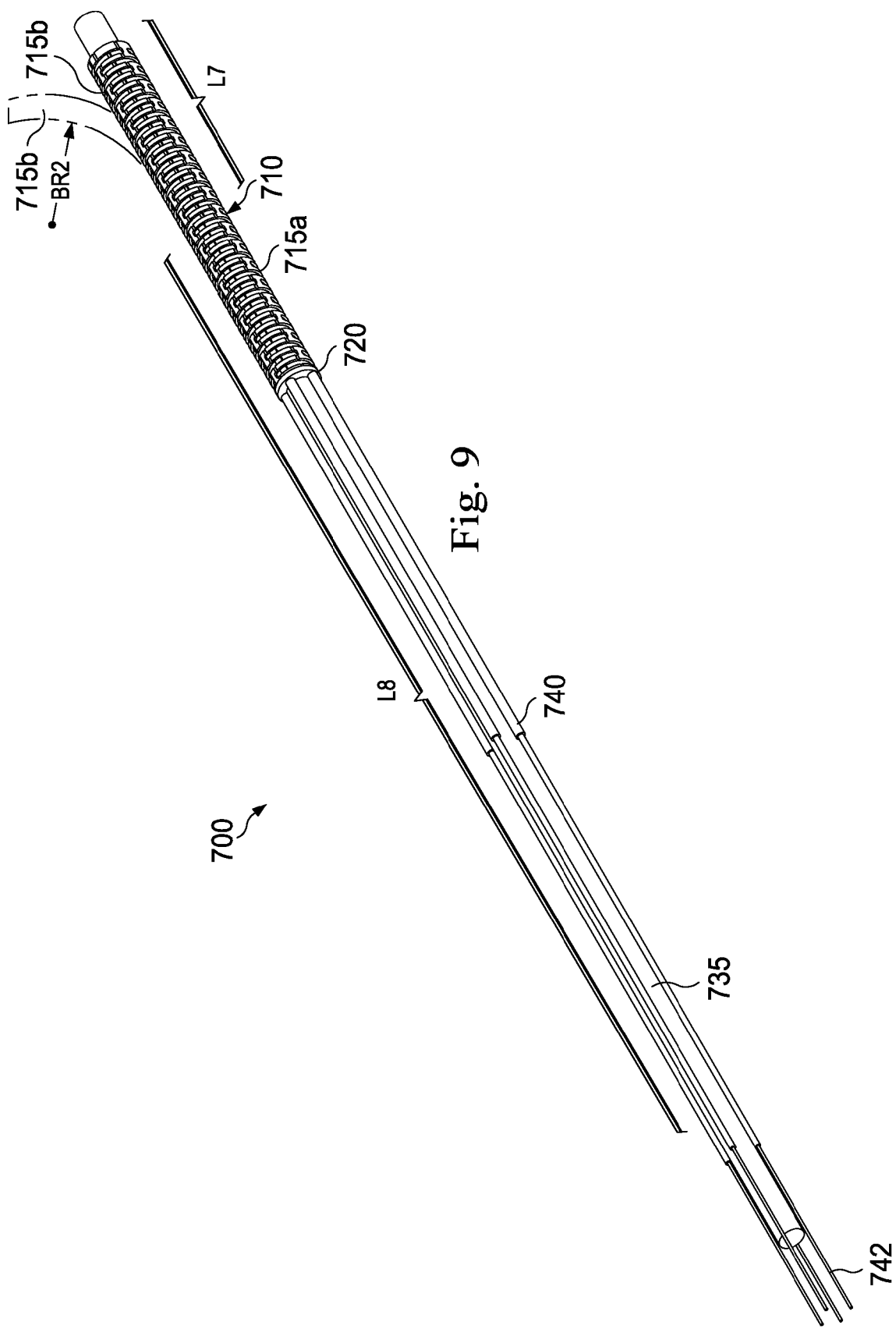

In the pictured embodiment, each cable assembly 314 includes two coil pipes 316, 320 of varying diameters and varying termination locations. In some embodiments, the coil pipes 316, 320 may be wound in opposite directions, or counterwound. The coil pipes 316, 320 can free float with respect to each other. In other words, as shown in FIG. 9, the two separate, nested coil pipes 316, 320 are arranged to have a space between them and can freely shift along a common longitudinal axis LA with respect to each other. In some embodiments, the coil pipes 316, 320 may be coated in a lubricant or friction-minimizing material such as, by way of non-limiting example, polytetrafluoroethylene (PTFE). The two separate coil pipes 316, 320 allow each cable assembly 314 to articulate two different lengths of the distal portion 304 of the catheter system 300. Other embodiments may include any number of nested coil pipes having varying diameters and termination locations (e.g., each cable assembly may have more than two sets of nested coil pipes), thereby enabling a greater number of different articulable lengths of the catheter system 300.

In the pictured embodiment, as mentioned above, the inner coil pipes 316 terminate at the distal transition section 306b in approximately a common plane perpendicular to the lumen 310, and the outer coil pipes 320 terminate at the proximal transition section 306a in approximately a common plane perpendicular to the lumen 310. As shown in FIG. 3A, the outer coil pipes 320 terminate in the wall 305 where the outer coil pipes 320 are embedded or anchored to a proximal termination element 330 within the proximal transition section 306a of the wall 305. Similarly, the inner coil pipes 316 terminate in the wall 305 where the inner coil pipes 316 are embedded or anchored to a distal termination element 332 within the distal transition section 306b of the wall 305. The proximal and distal termination elements 330, 332 may comprise any of a variety of structures configured to anchor or bind the outer and inner coil pipes 320, 316, respectively. For example, by way of non-limiting example, the distal termination elements 330, 332 may comprise rigid rings, flexible rings, and/or discrete anchoring structures within the wall 305. Alternatively, rather than rigidly fixing the proximal and distal ends of the coil pipes within the walls or anchoring rings, the walls or anchoring rings may serve to block distal movement of the coil pipe. For example, a ring may serve as a proximal termination element 330. The ring has apertures large enough to allow passage of the tendon, but not the coil pipe through which the tendon extends. The coil pipe is in abutment with the ring 300 but may not be fixed to the ring. Nevertheless, the ring 300 prevents the distal movement of the coil pipe when the coil pipe is under a load. In various embodiments, the proximal and distal termination elements may be generally parallel or non-parallel to each other.

In the pictured embodiment, a distal end 340 of each outer coil pipe 320 is directly secured to the proximal termination element 330 proximal to the steerable section 307, and a distal end 342 of each inner coil pipe 316 is directly secured to the distal termination element 332 proximal to the distal steerable portion 307b. In some embodiments, the coil pipes 316, 320 may have a surface treatment to aid in fixation to the termination elements 332, 330. In some embodiments, the distal ends 340, 342 of each coil pipe 320, 316, respectively, may be secured to the termination elements 330, 332, respectively, via, by way of non-limiting example, an adhesive or melting. As described above, in various embodiments, the elements 330, 332 may not fixedly terminate the distal ends of the coil pipes, but rather may create an abutment surface that blocks movement of the coil pipes when a load is applied. In some embodiments, the distal ends 340, 342 of the coil pipes 320, 316, respectively, are not anchored to any discrete termination elements, such as rigid rings, within the flexible wall 305 or the catheter system 300. Rather, each coil pipe 320, 316 terminates within and is affixed to the wall 305 at a position proximal to whichever steerable section of the distal portion 304 is configured to be steered by the tendon 318 carried within the particular cable assembly 314.

Therefore, if the outer coil pipes 320 are selectively axially constrained (e.g., via clamping) over the inner coil pipes 316, a resulting articulable length L1 of the catheter system 300 would include the length of the catheter system 300 distal to the proximal termination element 330 (i.e., the proximal and distal steerable portions 307a, 307b). If, however, the inner coil pipes 316 are axially constrained (e.g., via clamping), a resulting articulable length L2 of the catheter system 300 would include the length of the catheter system 300 distal to the distal termination element 332 (i.e., only the distal steerable portion 307b). Thus, as shown more clearly in FIGS. 8 and 9, the inner and outer coil pipes 316, 320 comprise axially variable stiffening mechanisms that are adjustable between a first state in which an actuation of the control tendon 318 produces a first bend radius in the steerable distal section and a second state in which the actuation of the control tendon 318 produces a second bend radius, different from the first bend radius, in the steerable distal portion 314.

Although the coil pipes 316, 320 in the pictured embodiment terminate at two separate common planes at the distal transition section 306b and the proximal transition section 306a, respectively, it should be understood that an individual coil pipe could extend into any length of the catheter system 300 (e.g., the flexible body 216) with the coil pipes terminating at different lengths (i.e., not in a common plane). For example, in the embodiments like that shown in FIG. 3A, the coil pipes 316, 320 extend only partially along the length of the catheter system 300. In other embodiments, at least one set of the coil pipes 316, 320 extends the entire length or substantially the entire length of the catheter system 300 (e.g., to a distal-most steerable segment within the distal portion 304).

Figure 3B:
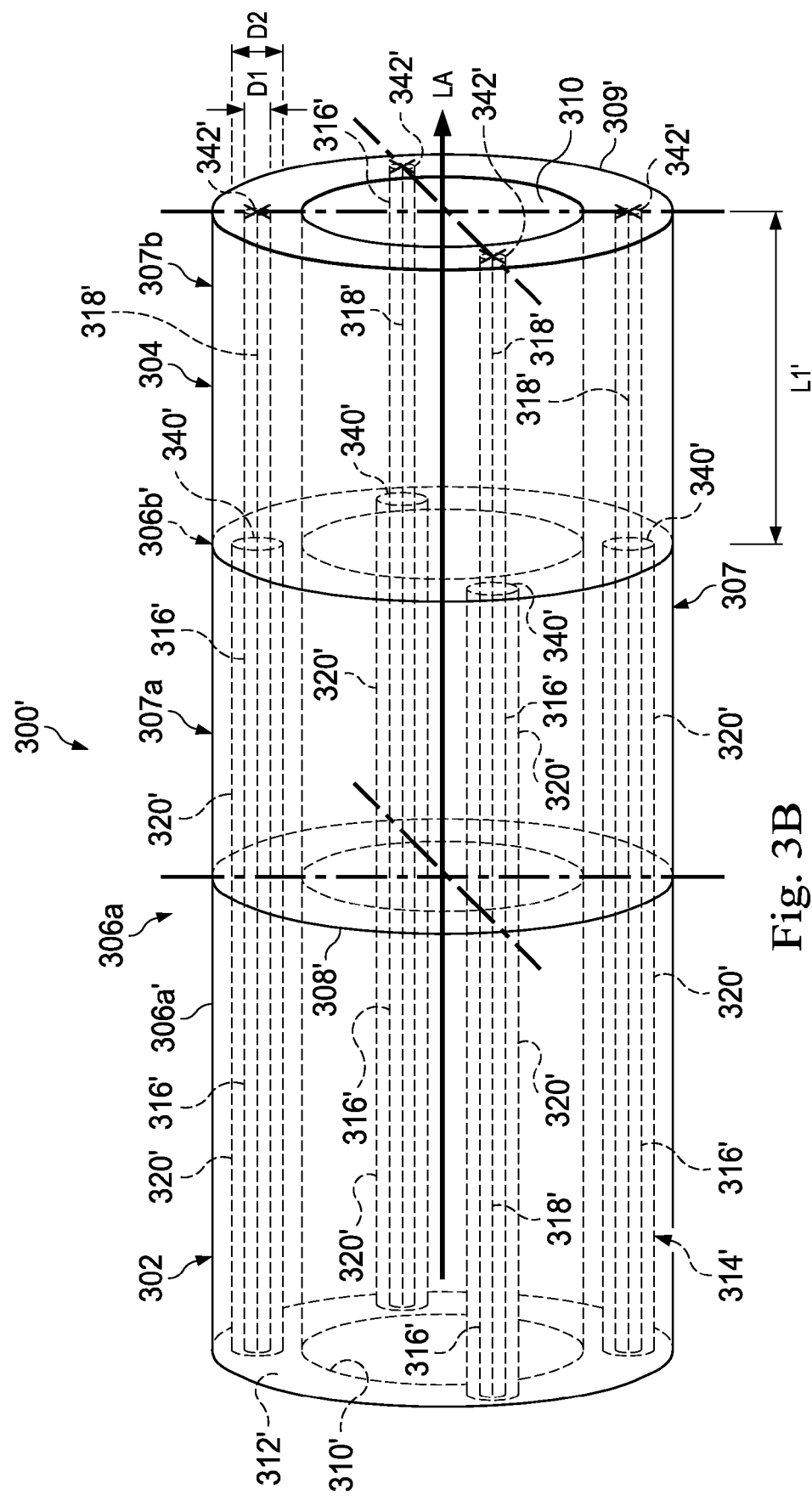
FIG. 3B illustrates an exemplary catheter system, showing relative positions of various elements that enable articulation of the system, in accordance with an embodiment of the present disclosure.

For example, in an exemplary catheter system 300' shown in FIG. 3B, the inner coil pipes 316' extend substantially the entire length of the catheter system 300' and terminate at a common plane defined by the distal end 309'. The catheter system 300' is substantially similar to the catheter system 300 described above in relation to FIG. 3 except for the differences in coil pipe termination positions described herein. In particular, in the pictured embodiment, the outer coil pipes 320' extend past the proximal transition section 306' to terminate at the distal transition section 306b' within the distal portion 304', proximal to the distal steerable portion 307b'. The inner coil pipes 316' extend out of the outer coil pipes 320' at the distal transition section 306b', extend through the distal steerable portion 307b', and attach to the distal end 309'. In the pictured embodiments, the inner coil pipes 316' extend the entire length of the tendons 318' within the steerable distal portion 304'. Thus, when the inner coil pipes 316' are axially constrained (e.g., via clamping), the entire steerable distal portion 304' is stiffened, thereby preventing articulation of both the proximal steerable portion 307a' and the distal steerable portion 307b'. In contrast, when the outer coil pipes 320' are axially constrained, only the more proximal portion of the distal portion 304', i.e., the proximal steerable portion 307a', is stiffened, resulting in an articulable length L1' including the length of the distal steerable portion 307b' (e.g., extending from the distal transition section 306b' to the distal end 309').

FIG. 4 is illustrates an exemplary catheter system 400 according to one embodiment of the present disclosure. The catheter system 400 may be the same as the catheter system 300 described above in relation to FIG. 3A. In particular, FIG. 4 shows a part of a proximal portion 402 and the entire distal portion 404 of the catheter system 400. The distal portion 404 comprises a steerable portion of the catheter system 400. The catheter system 400 includes a distal termination element 410, which divides the distal portion 404 into a proximal steerable portion 415a and a distal steerable portion 415b, and a proximal termination element 420. The proximal steerable portion 415a extends from the proximal termination element 420 to the distal termination element 410, and the distal steerable portion 415b extends from the distal termination element 410 to a distal end 425 of the catheter system 400. In the pictured embodiment, the catheter system 400 includes a soft distal tip 430, which may assist in minimizing inadvertent trauma to patient tissue as the catheter system 400 is advanced within the patient's anatomy.

The catheter system 400 includes a plurality of cable assemblies, each of which includes an inner coil pipe (not shown) nested within an outer coil pipe (not shown) that are coaxially aligned along the length of the catheter system 400. In the pictured embodiment, the inner coil pipes extend through a wall of the catheter system 400 into the distal portion 404 and terminate at the distal termination element 410, proximal to the distal steerable portion 415b. The outer coil pipes extend through a wall of the catheter system 400 through the proximal portion 402 and terminate at the proximal termination element 420, proximal to the distal portion 404, including both the proximal steerable portion 415a and the distal steerable portion 415b.

Thus, if the outer coil pipes are selectively axially constrained (e.g., clamped) a resulting articulable length L3 of the catheter system 300 would include the length of the catheter system 400 distal to the proximal termination element 420 (i.e., the proximal and distal steerable portions 415a, 415b). If, however, the inner coil pipes are axially constrained (e.g., clamped), a resulting articulable length L4 of the catheter system 400 would include the length of the catheter system 400 distal to the distal termination element 410 (i.e., only the distal steerable portion 415b).

Figure 5:
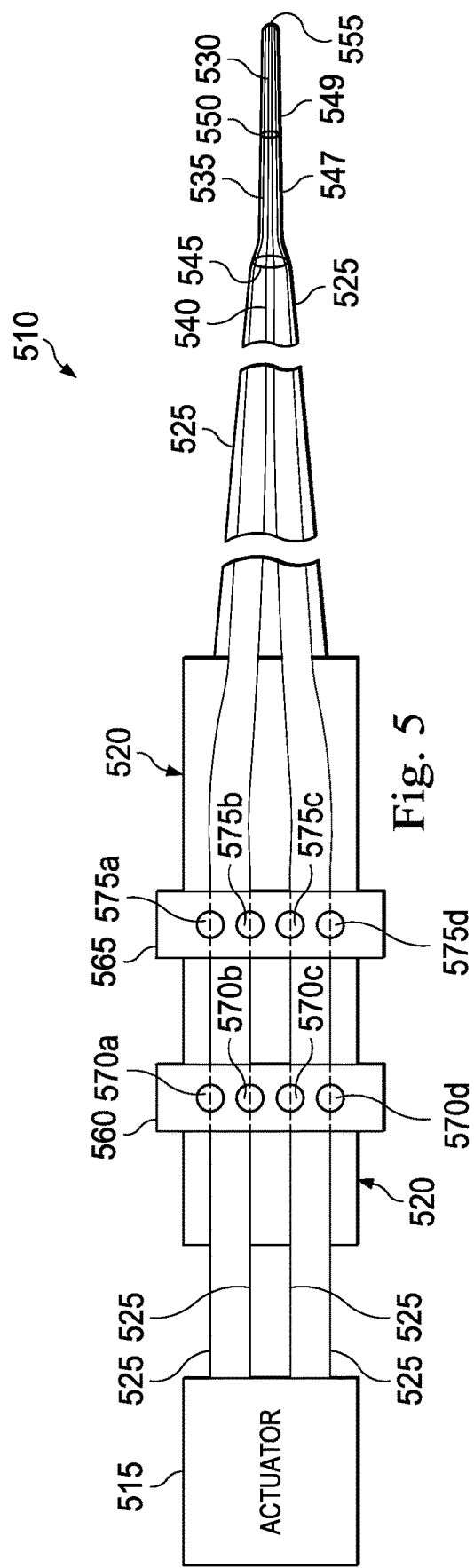
FIG. 5 illustrates a diagrammatic representation of an exemplary interventional instrument system including an exemplary catheter system according to one embodiment of the present disclosure.

FIG. 5 illustrates a diagrammatic representation of an interventional instrument system 500 including an exemplary catheter system 510 according to one embodiment of the present disclosure. The interventional instrument system 500 may be the same as the interventional instrument system 200 described above in relation to FIG. 2, and the catheter system 510 may be the same as the catheter system 300 described above in relation to FIG. 3A. The interventional instrument system 500 includes an actuator 515 and an instrument body 520 in addition to the catheter system 510. In some instances, the actuator 515 may be disposed within or integral with the instrument body 520. The various components of the interventional instrument system 500 are not drawn to scale with respect to each other, and the instrument body 520 is shown enlarged for illustrative purposes. Although the instrument body 520 is shown as a simplified tube-like structure in the pictured embodiment, the instrument body 520 may have any of a variety of shapes and configurations designed to enable a controller (e.g., a user or a robotic arm) to manipulate the catheter system 510.

Cable assemblies 525 extend from the actuator 515, through the instrument body 520, and into the catheter system 510. Each cable assembly 525 includes nested coil pipes that house at least one control cable or tendon 530, as described above in relation to FIGS. 3 and 4. For example, in the pictured embodiment, each cable assembly 525 includes the control tendon 530 extending through an inner coil pipe 535, which is nested within an outer coil pipe 540. The tension applied to the tendon 530 by the actuator 515 is isolated to a particular segment of the catheter system 510 through the use of the coil pipes 535, 540. These cable assemblies 525 can be actuated remotely and can be used to selectively apply force to and articulate discrete segments. The tendons 530 may be made from any of a variety of materials, including without limitation, stainless steel, titanium, Nitinol, ultra-high molecular weight polyethylene, and any other suitable material known to the skilled artisan. In some embodiments, the cable assemblies 525 are substantially similar in construct and in operation to the cables disclosed in U.S. Patent Application No. 2009/0099420 A1, entitled "System for Managing Bowden Cables in Articulating Instruments," filed Oct. 11, 2007, and published on Apr. 16, 2009, which is incorporated by reference herein in its entirety.

The outer coil pipes 540 extend from the actuator 510 to a proximal termination element 545 of the catheter system 510, halting proximally of a proximal steerable portion 547 and a distal steerable portion 549. The inner coil pipes 535 extend from the actuator 510 to a distal termination element 550 of the catheter system 510, halting proximally of the distal steerable portion 549. The control tendons 530 continue past the distal termination element 550 (and the distal ends of the inner coil pipes 535) to end at a distal end 555 of the catheter system 510. In some embodiments, the control tendons 530 may terminate proximal to the distal end 555. The inner and outer coil pipes 535, 540 may be substantially the same as the inner and outer coil pipes 316, 320, respectively, shown in FIG. 3A. The proximal and distal termination elements 545, 550 may be substantially the same as the proximal and distal termination elements 330, 332, respectively, shown in FIG. 3A.

The instrument body 520 can include axial control elements, such as, by way of non-limiting example, control clamps, that contact and interact with the different coil pipes of the cable assemblies 525. For example, in the pictured embodiment, the instrument body 520 includes two different axial control elements or control clamps, the proximal control clamp 560 and the distal control clamp 565. The control clamps 560, 565 may be controlled or adjusted by a user (e.g., manually) or by a telerobotic assembly (e.g., via computer-assistance or robotically). The control clamps 560, 565 may comprise any of a variety of structures configured to selectively clamp, compress, and/or tighten particular coil pipes 535, 540, and/or selectively constrict the particular lumen through which each separate set of coil pipes 535, 540 extend. Clamping the coil pipes 535, 540 substantially prevents the coil pipes from translating when under load thereby increasing the axial stiffness of the coil pipe when the tendon is tensioned. In the pictured embodiment, the proximal control clamp 560 interacts with the inner coil pipes 535, and the distal control clamp 565 interacts with the outer coil pipes 540. The proximal and distal control clamps 560, 565 each include a first state configured to increase the axial stiffness of the inner and outer coil pipes 535, 540, respectively. In some embodiments, clamping the coil pipe 535, 540 (e.g., by selectively transitioning the proximal and distal control clamps 560, 565, respectively, into the first state) axially compresses the coil pipe along its length (e.g., from the control clamps 560, 565 to the distal and proximal termination elements 550, 545, respectively).

Each control clamp 560, 565 includes a plurality of individual control features 570, 575, respectively. In the pictured embodiment, the control clamp 560 includes four different control features 570a, 570b, 570c, and 570d, and the control clamp 570 includes four different control features 575a, 575b, 575c, and 575d. Each individual control feature 570a-d and 575a-d is configured to interact with an individual coil pipe of the interventional instrument system 500. In particular, each control clamp 560, 565 includes at least one control feature 570, 575, respectively, that is configured to control movement in the pitch directions (or plane of motion) and at least one control feature 570, 575, respectively, that is configured to control movement in the yaw directions (or plane of motion). For example, in the pictured embodiment, the interventional instrument system 500 includes four control tendons 530a-d running through four separate cable assemblies 525a-d having inner coil pipes 535a-d and outer coil pipes 535a-d, 540a-d, respectively. The control features 570a-d are arranged to interact with the corresponding inner coil pipes 535a-d, respectively, and the control features 575a-d are arranged to interact with the corresponding outer coil pipes 540a-d.

Accordingly, each individual coil pipe may be adjusted independently of the others. For example, the outer coil pipe 540a may be axially constrained (e.g., clamped) while the inner coil pipe 535a remains unconstrained (e.g., unclamped). In other instances, the outer coil pipes 540a, 540c may be axially constrained (e.g., clamped), thus affecting tendons 530a, 530c, respectively, while the outer coil pipes 540b, 540d remain unconstrained (e.g., unclamped). This allows the controller (e.g., a user or a telerobotic assembly/control system) to assign different articulable lengths of the catheter system 500 in different directions of motion. For example, the controller may adjust the control clamps 560, 565 such that the articulable length of the catheter system 510 is greater in the x-y plane than in the x-z plane, or vice-versa.

Figure 6A:
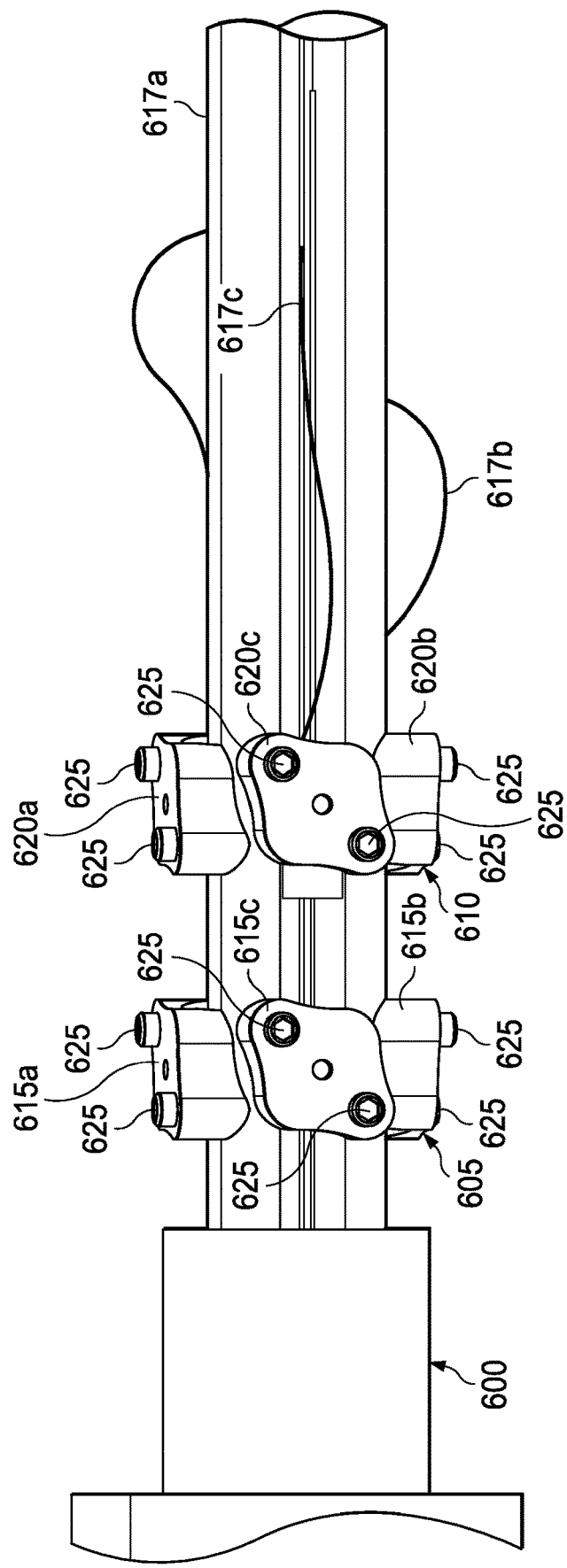
FIG. 6A is illustrates an exemplary instrument body according to one embodiment of the present disclosure.
Figure 6B:
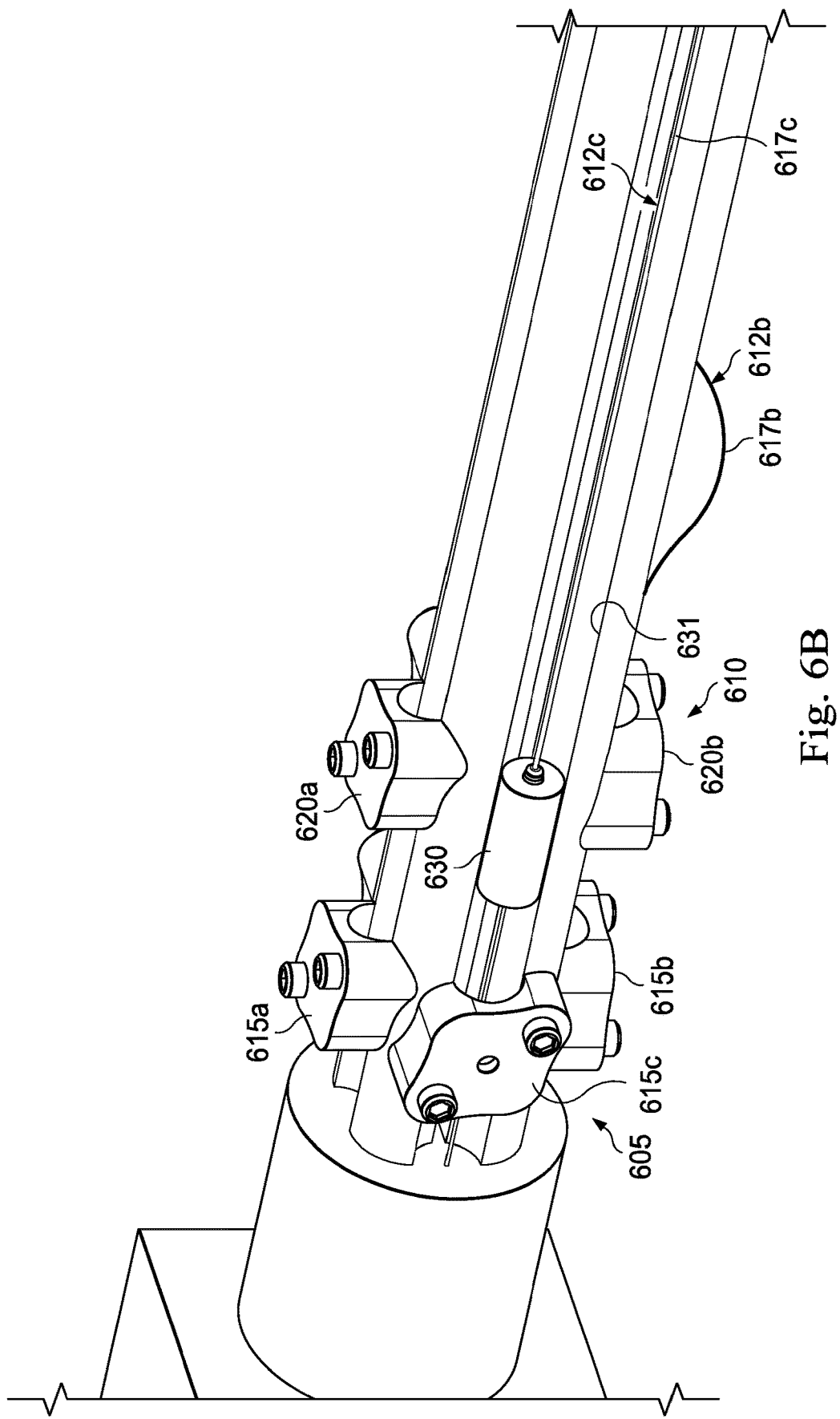
FIG. 6B is illustrates exemplary control elements on the exemplary instrument body shown in FIG. 6A according to one embodiment of the present disclosure.

FIGS. 6A and 6B illustrate an exemplary instrument body 600 according to one embodiment of the present disclosure. The instrument body 600 may substantially similar to the instrument body 520 described above in relation to FIG. 5. The instrument body 600 includes a first control element 605 and a second control element 610, each of which are associated with cable assemblies (not shown) extending through the instrument body 600. Each cable assembly includes nested inner coil pipes (not shown) and outer coil pipes 617a-c (a fourth coil pipe is not shown due to in FIG. 6A) which surround a control tendon. In the pictured embodiment, each control element 605, 610 controls the inner and outer coil pipes, respectively, and includes at least four individual control features 615a-c and 620a-c, respectively. Each individual control feature 615a-c contacts and controls an individual inner coil pipe. Similarly, each individual control feature 620a-c contacts and controls an individual outer coil pipe 617a-c, respectively. In the pictured embodiment, each control feature 615a-c, 620a-c includes screws 625 that can be individually adjusted (e.g., tightened or loosened) by the controller to selectively adjust the axial stiffness of the inner and outer coil pipes, respectively. In the pictured embodiment, the inner and outer coil pipes comprise axially variable stiffening mechanisms that are adjustable between a first state (i.e., in which either the inner or outer coil pipes are axially constrained (e.g., via tightening of the screws 625)) in which an actuation of the control tendon produces a first bend radius in the steerable distal section and a second state (i.e., in which the other of the inner or outer coil pipes are axially constrained) in which the actuation of the control tendon produces a second bend radius, different from the first bend radius, in the steerable distal portion.

FIG. 6B illustrates the instrument body 600 with the control feature 620c removed to expose a grip element 630, which is disposed about the cable assembly 612c. In the pictured embodiment, the grip element 630 comprises an axially movable cylinder that is coupled to the cable assembly 612c and is positioned within a groove 631. The grip element 630 can translate axially within the groove 631. In other embodiments, the grip element 630 can comprise any of a variety of coupling structures capable of compressing or constraining the axial motion of the desired coil pipe (in this case, the outer coil pipe 617c) when force is applied to the grip element 630. In the pictured embodiment, the controller may adjust the control feature 620c to apply force to the grip element 630 (e.g., to apply a transverse load to the grip element 630), which then compresses or constrains the axial motion of a proximal end of the outer coil pipe 617c. Thus, adjustment of the control feature 620c may halt the axial translation of the grip element 630 by applying a transverse force or load on the grip element 630, thereby preventing the axial translation of the proximal end of the outer coil pipe 617c, which stiffens the catheter system along the length of the outer coil pipe 617c. When the outer coil pipe 617c is compressed, the articulable lengths of the catheter system and the effects of actuation of the tendon within that coil pipe (not shown) change accordingly, depending upon the termination location of the outer coil pipe 619c. In some embodiments, the grip element 630 is sized relative to the control feature 620c to allow for adequate restriction of axial motion of the grip element 630. For example, the grip element 630 and the control feature 620c may share a common axial length. In other embodiments, the grip element may comprise any size and shape of structure coupled to a proximal portion of a coil pipe and configured to limit or otherwise control the axial translation of the coil pipe. Other embodiments may lack a grip element, and may be configured to axially compress or constrain the axial motion of a proximal end of the desired coil pipe in another way upon adjustment of the corresponding control feature. In various alternative embodiments, the axial control element may be a barrier placed proximally of the coil pipe to prevent the coil pipe from translating when under load.

FIG. 7 illustrates a perspective, partially cut-away view of an exemplary catheter system 700 according to one embodiment of the present disclosure. The catheter system 700 may be the same as the catheter system 300 described above in relation to FIG. 3A. In particular, FIG. 7 shows a part of a proximal portion 702 (in a partially cut-away view for illustrative purposes) and the entire distal portion 704 of the catheter system 700. The distal portion 704 comprises a steerable or articulable portion of the catheter system 700.

The distal portion 704 may comprise any of a variety of elongate structures, including, without limitation, an elongate tube having a plurality of cut-out features lending flexibility or a series of linearly-arranged links connected by link pivots (e.g., hinge joints). The catheter system 700 includes a distal termination element 710, which divides the distal portion 704 into a proximal steerable portion 715a and a distal steerable portion 715b, and a proximal termination element 720. The proximal steerable portion 715a extends from the proximal termination element 720 to the distal termination element 710, and the distal steerable portion 715b extends from the distal termination element 710 to a distal end 425 of the catheter system 700.

The catheter system 700 includes a plurality of cable assemblies 730, each of which includes a first or inner coil pipe 735 nested within a second or outer coil pipe 740 that are coaxially aligned along the length of the catheter system 700. Each cable assembly 730 also includes a control tendon 742, which extends through the inner coil pipe 735. In the pictured embodiment, the inner coil pipes 735 extend through a wall (not shown) of the catheter system 700 into the distal portion 704 and terminate at the distal termination element 710, proximal to the distal steerable portion 715b. The outer coil pipes 740 extend through a wall of the catheter system 700 through the proximal portion 702 and terminate at the proximal termination element 720, proximal to the distal portion 704, including both the proximal steerable portion 715a and the distal steerable portion 715b.

In the pictured embodiment, the catheter system 700 includes a distal tip 728 extending past the tendons, which terminate at the distal end 425. In some embodiments, the distal tip 728 comprises a soft and/or pliable tip configured to reduce trauma to patient tissue as the catheter system 700 is advanced through the patient's anatomy.

Figure 8:
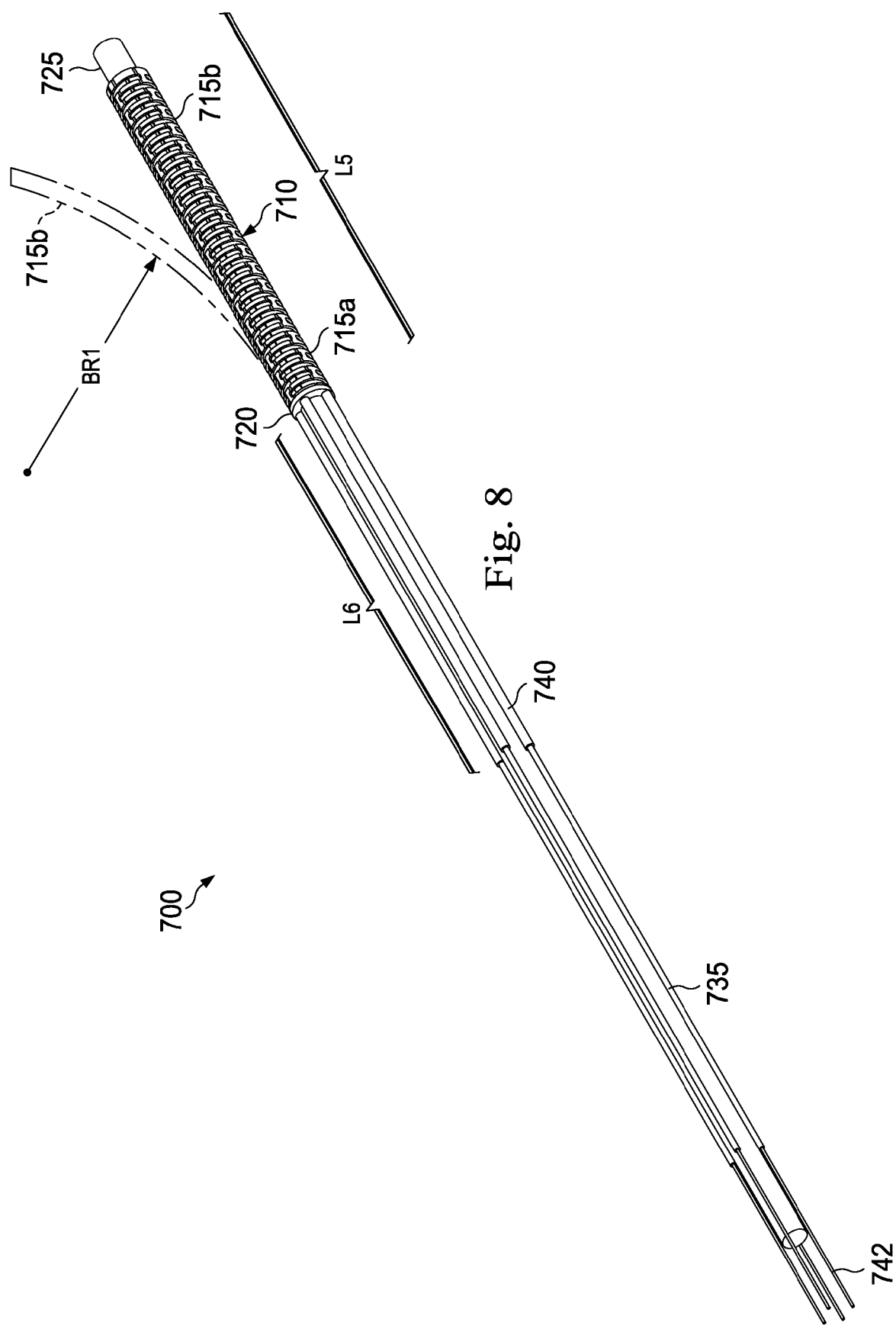
FIGS. 8 and 9 illustrate perspective, partially cut-away views of the exemplary catheter system shown in FIG. 7, shown having varying articulable lengths.

Accordingly, as shown in FIG. 8, if the outer coil pipes 740 are selectively axially constrained (e.g., via clamping) over the inner coil pipes 735 (e.g., by a controller manipulating control elements at the instrument body), a resulting articulable length L5 of the catheter system 700 would include the parts of the catheter system 700 distal to the proximal termination element 720 (i.e., the proximal and distal steerable portions 715a, 715b). Moreover, the axial stiffness is increased along a length L6 of the catheter system 700 when the outer coil pipes 740 are axially constrained (e.g., via clamping). The length L6 includes the entire axially constrained length of the outer coil pipes 740. Constraining the coil pipes provides axial stiffness to the proximal shaft sufficient to prevent bending when the tendon is tensioned.

If, however, as shown in FIG. 9, the inner coil pipes 735 are axially constrained (e.g., via clamping), a resulting articulable length L7 of the catheter system 700 would include only the parts of the catheter system 700 distal to the distal termination element 710 (i.e., only the distal steerable portion 715b). Thus, any articulation can only occur distal to the termination points of the axially constrained set of coil pipes. The articulable length of the catheter system 700 can be adjusted by selectively axially constraining (e.g., via clamping) either the inner or outer coil pipes 735, 740, respectively. Moreover, the axial stiffness is increased along a length L8 of the catheter system 700 when the inner coil pipes 735 are axially constrained (e.g., via clamping). The length L6 includes the entire axially constrained length of the inner coil pipes 735.

As described briefly above in relation to FIG. 3A, the inner and outer coil pipes 735, 740 comprise axially variable stiffening mechanisms that are adjustable between a first state in which an actuation of the control tendon 742 produces a first bend radius (e.g., bend radius BR1 shown in FIG. 8) in the steerable distal section and a second state in which the actuation of the control tendon 742 produces a second bend radius (e.g., bend radius BR2, shown in FIG. 9), different from the first bend radius, in the steerable distal portion 704. As illustrated by FIGS. 8 and 9, the bend radius of the catheter system 700 is altered by the clamping of the different coil pipes (i.e., 735 and 740). In the shown example, the bend radius BR1 of the catheter system 700 when the outer coil pipes 740 are axially constrained (e.g., via clamping) is greater than the bend radius BR2 of the catheter system 700 when the inner coil pipes 735, or more distally-extending coil pipes, are axially constrained.

It should be understood that FIGS. 7-9 present partially cut-away views of the catheter system 700, and although the inner and outer coil pipes 735, 740, respectively, are not shown extending proximally toward an instrument body and an actuator, both the inner and outer coil pipes 735, 740, in actuality, will extend proximally over the control tendons 742 toward an instrument body and an actuator (e.g., the instrument body 520 and the actuator 510 shown in FIG. 5). Thus, the lengths L6 and L8 shown in FIGS. 8 and 9 may extend proximally toward an instrument body and an actuator (e.g., the instrument body 520 and the actuator 510 shown in FIG. 5) as well.

As mentioned above with respect to FIG. 5, each individual coil pipe may be adjusted independently of the others. For example, a set of opposite outer coil pipes 740 may be axially constrained (e.g., clamped) while the remaining outer coil pipes 740 remain unconstrained (e.g., unclamped), thus affecting one set of tendons 730 responsible for bending the distal portion 704 in one plane, without affecting the other set of tendons 730, which may be responsible for bending the distal portion in a different plane. This allows the controller (e.g., a user or a telerobotic assembly/control system) to assign different articulable lengths of the catheter system 700 in different planes of motion. For example, the controller may adjust the control clamps (e.g., the control clamps 560, 565 shown in FIG. 5) such that the articulable length of the catheter system 700 is greater in the x-y plane than in the x-z plane, or vice-versa. Thus, the selective axial constraining of the inner or outer coil pipes 735, 740, respectively, can control the articulable length as well as the desired directionality of the distal portion 704.

Figure 10:
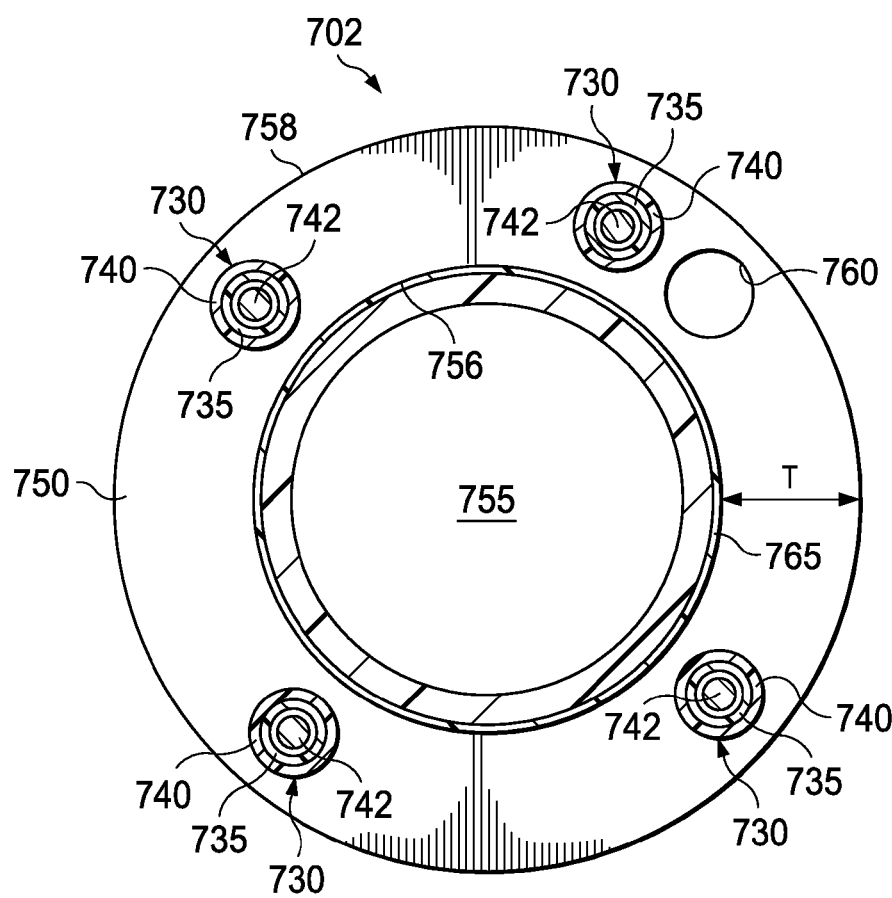
FIG. 10 illustrates a cross-sectional view of a proximal portion of the exemplary catheter system shown in FIG. 7.

FIG. 10 illustrates a cross-sectional view of the proximal portion 702 of the exemplary catheter system 700 pictured in FIG. 7. At the proximal portion 702, the catheter system 700 comprises a hollow cylindrical tube or wall 750 defining a lumen 755. In some embodiments, the lumen 755 is configured as a working channel for the passage of medical tools. Other embodiments may lack a lumen 755. The wall 750 comprises a length of flexible tubing with a thickness T extending from an inner surface 756 to an outer surface 758. In the pictured embodiment, the wall 750 carries includes five channels, including four cable assemblies 730 configured to carry the tendons 742, and an additional channel 760, which may be configured to carry additional tools or sensors, such as, by way of non-limiting example, a sensor element. The inner coil pipes 735 and the outer coil pipes 740 are disposed concentrically and co-axially about the tendons 742 within the wall 750. In some embodiments, the coil pipes include a wound element having either an open pitch or a closed pitch. In other embodiments, the coil pipes include a woven or braided element. In the pictured embodiment, the proximal portion 702 includes a support layer 765, which may be configured to help maintain the patency of the lumen 755. Other embodiments may include any number or arrangement of channels, support layers, and/or coil pipes relative to the lumen 755, depending upon the application and structure of the catheter system 700.

In some embodiments, the cable assemblies 730 are configured to maintain the patency or openness of the lumen 755 and minimize friction such that (1) the inner coil pipes 735 can slide freely or float within the outer coil pipes 740, and (2) the tendons 742 can slide freely or float within the inner coil pipes 735. In some embodiments, the cable assemblies 730 are configured to provide reliable positioning of the tendons 742 along the length of the catheter system 700. The coil pipes 735, 740 may be constructed of any a variety of flexible materials, including without limitation, nylon, polyimide, PTFE, Pebax, and any other suitable material known to the skilled artisan. The coil pipes 735, 740 may be constructed with a coil or braided structure.

In some embodiments, the wall 750 is configured to maintain the cable assemblies 730 in a substantially known radial position (e.g., a constant radial distance from the longitudinal axis LA extending through the center of the lumen 755, as shown in FIG. 3A) through the length of or at least a portion of the length of the catheter system 700. This may allow for a reliable correlation between the shape and orientation of sensory elements extending through the catheter system 700 and the shape and orientation of the catheter system 700. In some embodiments, the radial position of the cable assemblies 730 vary along the length of the proximal portion 702, relative to the inner surface 756 and the outer surface 758. For example, in some embodiments, the cable assemblies 730 may shift closer to the outer surface 758 as the cable assemblies 730 extend distally through the catheter system 700 toward the distal portion 704.

Figure 11:
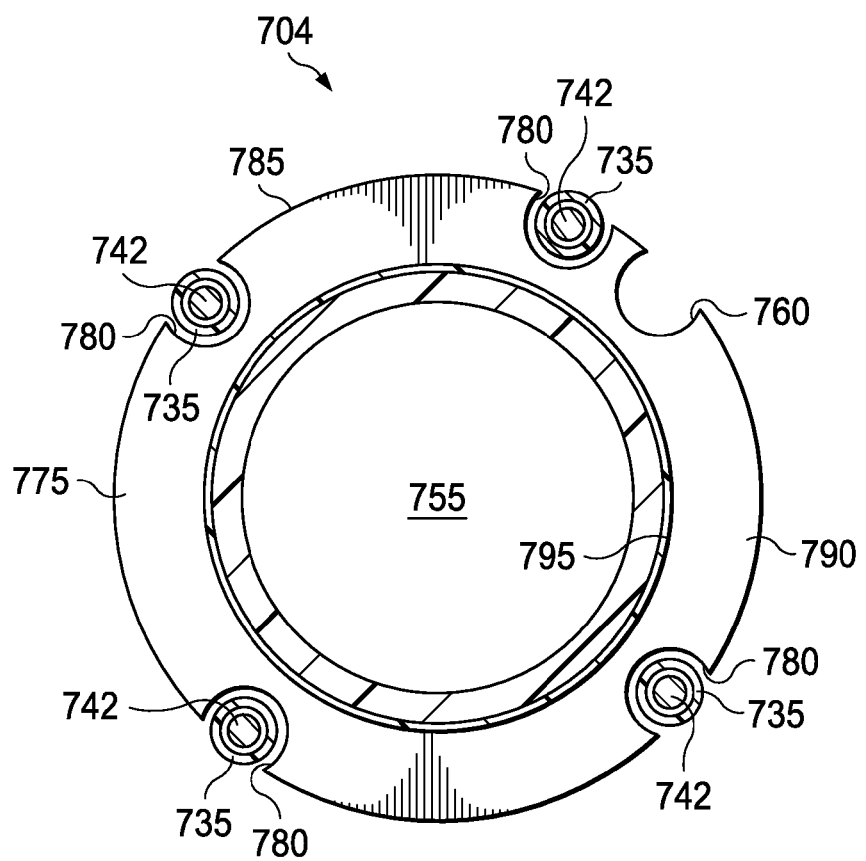
FIG. 11 illustrates a cross-sectional view of a distal portion of the exemplary catheter system shown in FIG. 7.

FIG. 11 illustrates a cross-sectional view of the distal portion 704 of the exemplary catheter system 700 pictured in FIG. 7. In particular, FIG. 11 illustrates a cross-sectional view of the distal portion 704 at or proximal to the distal termination element 710 shown in FIG. 7 (i.e., where the inner coil pipes 735 terminate or anchor). As mentioned above, the distal portion 704 comprises a steerable or articulable portion of the catheter system 700. The distal portion 704 may comprise any of a variety of elongate structures, including, without limitation, an elongate, steerable tube 775 having a plurality of cut-out features lending flexibility or a series of linearly-arranged links connected by link pivots (e.g., hinge joints). As illustrated by FIG. 11, the tendons 742 and the inner coil pipes 735 continue into the distal portion 704 (i.e., into the proximal steerable portion 715a of the distal portion 704). In the embodiment shown in FIG. 11, the tendons 742 and the inner coil pipes 735 extend within grooves 780 disposed on an outer surface 785 of the tube 775. In other embodiments, the tendons 742 and the inner coil pipes 735 may be disposed within a wall 790 of the tube 775, between an inner surface 795 and the outer surface 785.

The steerable tube 775 may be made of any suitable biocompatible material that provides the requisite tensile and flexural properties. Suitable materials may include, by way of non-limiting example, shape memory material such as Nitinol, stainless steel, and plastics. In some embodiments, the steerable tube 775 is made from the same material throughout. In other embodiments, the steerable tube 775 may be made from two or more different materials (e.g., stainless steel in a less flexible zone and Nitinol in a more flexible zone). One technique for the construction of the steerable tube 775 is laser cutting technology, which may produce the steerable tube 775 in an automatic fashion (e.g., by computer numeric controlled cutting). Fine changes in the wall thickness, the length, an inner diameter, and an outer diameter of the tube 775 may be automatically programmed and generated using laser cutting technology. Other suitable manufacturing methods may include, by way of non-limiting example, water jet cutting, electrochemical etching, electrical discharge machining, and diamond cutting.

The embodiment disclosed herein provide for a single instrument or catheter system that is configured to provide at least two different articulable lengths having different bend radii, which may be suitable for applications requiring tools having varying radii of curvature (e.g., to navigate the branching, progressively narrower bronchial passageways of a patient). Moreover, the nested coil pipes disclosed herein act as an axially adjustable stiffening mechanism configured to increase the axial stiffness of various lengths of a single catheter system.

One or more elements in embodiments of the invention may be implemented in software to execute on a processor of a computer system such as control system 112. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, intranet, etc.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A minimally invasive medical instrument comprising:
   an elongate flexible body including a proximal portion, a distal portion, and a distal end;
   a tendon extending from the proximal portion through the distal portion of the elongate flexible body, the tendon being actuatable to bend the distal portion;
   a nested conduit extending through the elongate flexible body along a longitudinal axis, wherein the nested conduit includes:
      an outer conduit; and
      an inner conduit disposed inside the outer conduit and having an inner lumen such that the tendon extends through the inner conduit, wherein each of the outer conduit and the inner conduit is axially compressible;
   a first control element coupled to the outer conduit; and
   a second control element coupled to the inner conduit, wherein each of the first control element and the second control element is adjustable between a first state and a second state, wherein the outer conduit is axially constrained proximate the first control element in the first state of the first control element, wherein the outer conduit is not axially constrained proximate the first control element in the second state of the first control element, wherein the inner conduit is axially constrained proximate the second control element in the first state of the second control element, wherein the inner conduit is not axially constrained proximate the second control element in the second state of the second control element, and wherein an articulatable length of the nested conduit is variable based on adjustment between the first and second states of the first control element and based on adjustment between the first and second states of the second control element.

2. The minimally invasive medical instrument of claim 1, wherein the inner conduit extends through the proximal portion and distal portion; and
   the outer conduit extends through the proximal portion.

3. The minimally invasive medical instrument of claim 2, further comprising a proximal termination element disposed between the proximal portion and the distal portion, wherein the outer conduit terminates at the proximal termination element.

4. The minimally invasive medical instrument of claim 3, further comprising a distal termination element disposed between the distal portion and the distal end, wherein the inner conduit terminates at the distal termination element.

5. The minimally invasive medical instrument of claim 4, wherein the distal portion comprises a proximal steerable portion extending between the proximal termination element and the distal termination element of the elongate flexible body.

6. The minimally invasive medical instrument of claim 5, further comprising a plurality of first control elements each coupled to the inner conduit and spaced apart from each other along the longitudinal axis and a plurality of second control elements each coupled to the outer conduit and spaced apart from each other along the longitudinal axis.

7. The minimally invasive medical instrument of claim 6, wherein the proximal steerable portion is configured to be inflexible when each of the plurality of first control elements is in the first state.

8. The minimally invasive medical instrument of claim 7, wherein the distal portion comprises a distal steerable portion extending between the distal termination element and the distal end of the elongate flexible body.

9. The minimally invasive medical instrument of claim 8, wherein the distal steerable portion is configured to be flexible when each of the plurality of first control elements is in the first state.

10. The minimally invasive medical instrument of claim 1 wherein at least one of the inner conduit or the outer conduit comprises a plurality of coils and wherein at least one of the first control element or the second control element is configured to axially constrain the at least one of the inner conduit or the outer conduit in the first state by one of axially compressing the at least one of the inner conduit or the outer conduit until the plurality of coils of the at least one of the inner conduit or the outer conduit physically contact each other or radially compressing the at least one of the inner conduit or the outer conduit.

11. A minimally invasive medical instrument comprising:
an elongate flexible body including a proximal portion, an intermediate portion coupled to the proximate portion at a proximal transition, and a distal end coupled to the intermediate portion at a distal transition;
an outer conduit extending through the elongate flexible body and coupled to the proximal transition;
an inner conduit extending through the elongate flexible body within the outer conduit and coupled to the distal transition, wherein each of the outer conduit and the inner conduit is axially compressible;
a first control element coupled to the outer conduit; and
a second control element coupled to the inner conduit, wherein each of the first control element and the second control element is adjustable between a first state and a second state, wherein the outer conduit is axially constrained proximate the first control element in the first state of the first control element, wherein the outer conduit is not axially constrained proximate the first control element in the second state of the first control element, wherein the inner conduit is axially constrained proximate the second control element in the first state of the second control element, wherein the inner conduit is not axially constrained proximate the second control element in the second state of the second control element, and wherein an axial stiffness of at least a first portion of the elongate flexible body when at least one of the inner conduit or the outer conduit is axially constrained is greater than the axial stiffness of the at least the first portion of the elongate flexible body when the at least one of the inner conduit or the outer conduit is not axially constrained.

12. The minimally invasive medical instrument of claim 11, wherein the inner conduit includes a coil pipe, and wherein at least a portion of the coil pipe is in contact with an adjoining portion of the coil pipe when the inner conduit is axially constrained.

13. The minimally invasive medical instrument of claim 11 further comprising a tendon extending through the elongate flexible body within the inner conduit.

14. The minimally invasive medical instrument of claim 13, wherein the first control element is configured to apply a compression such that an actuation of the tendon produces a first bend radius when the inner conduit is axially constrained and a second bend radius that is different from the first bend radius when the inner conduit is not axially constrained.

15. The minimally invasive medical instrument of claim 11, wherein the first control element is a first plurality of first control elements, and wherein the second control element is a second plurality of second control elements,
wherein each of the second plurality of second control elements is adjustable to apply a compression to the outer conduit to change the outer conduit between axially constrained and not axially constrained, and
wherein the second plurality of second control elements is adjustable independent of the first plurality of first control elements.

16. The minimally invasive medical instrument of claim 11, wherein the intermediate portion is configured such that a flexibility of the intermediate portion depends on an axial stiffness of the inner conduit.

17. The minimally invasive medical instrument of claim 11, wherein the proximal portion is configured such that a flexibility of the proximal portion depends on an axial stiffness of the outer conduit.

18. The minimally invasive medical instrument of claim 1, further comprising at least one grip element coupled to the nested conduit, wherein at least one of the first control element or the second control element is configured to inhibit translational motion of the at least one grip element in the first state by applying a radial compression to the at least one grip element and permit translational motion of the at least one grip element in the second state.

19. The minimally invasive medical instrument of claim 18, wherein at least one of the first control element or the second control element comprises at least one screw that is adjustable by a controller in operative communication with the at least one of the first control element or the second control element to selectively inhibit or permit translational motion of the at least one grip element.

20. The minimally invasive medical instrument of claim 1, wherein the tendon comprises a first tendon, and the minimally invasive medical instrument further comprising:
a second tendon;
a second nested conduit, wherein the second nested conduit includes:
a second outer conduit; and
a second inner conduit disposed inside the second outer conduit and having a second inner lumen such that the second tendon extends through the second inner conduit;
a third control element coupled to the second outer conduit; and
a fourth control element coupled to the second inner conduit, wherein each of the third control element and the fourth control element is adjustable between the first state and the second state,
wherein the first control element and the third control element are independently adjustable between their respective first and second states.

* * * * *